(12) United States Patent
De Boer et al.

(10) Patent No.: US 7,304,159 B2
(45) Date of Patent: Dec. 4, 2007

(54) LIGANDS AND CATALYST SYSTEMS THEREOF FOR ETHYLENE OLIGOMERISATION TO LINEAR ALPHA OLEFINS

(75) Inventors: Eric Johannes Maria De Boer, Amsterdam (NL); Harry Van Der Heijden, Amsterdam (NL); Wilhelmina Cornelia Verhoef-Van Wijk, Amsterdam (NL); Arie Van Zon, Amsterdam (NL)

(73) Assignee: Shell Oil Company, Houston, TX (US)

( * ) Notice: Subject to any disclaimer, the term of this patent is extended or adjusted under 35 U.S.C. 154(b) by 339 days.

(21) Appl. No.: 11/080,170

(22) Filed: Mar. 15, 2005

(65) Prior Publication Data

US 2005/0159601 A1    Jul. 21, 2005

Related U.S. Application Data

(62) Division of application No. 10/208,535, filed on Jul. 30, 2002, now Pat. No. 7,049,442.

(30) Foreign Application Priority Data

Aug. 1, 2001 (EP) ................... 01306607

(51) Int. Cl.
C07D 213/53 (2006.01)
C07D 401/12 (2006.01)
C07D 402/12 (2006.01)
C07D 217/12 (2006.01)
C07C 2/24 (2006.01)

(52) U.S. Cl. ............. 546/268.1; 546/112; 546/276.4; 546/329; 585/527

(58) Field of Classification Search ............ 546/329, 546/276.4, 268.1, 112; 585/527
See application file for complete search history.

(56) References Cited

U.S. PATENT DOCUMENTS

| | | | |
|---|---|---|---|
| 4,728,583 A | 3/1988 | Yamazaki et al. | 428/690 |
| 4,822,911 A | 4/1989 | Fried | 560/205 |
| 4,912,333 A | 3/1990 | Roberts et al. | 250/487.1 |
| 4,944,026 A | 7/1990 | Arakawa et al. | 250/484.1 |
| 5,151,604 A | 9/1992 | Kohda et al. | 250/484.1 |
| 5,318,935 A | 6/1994 | Canich et al. | 502/117 |
| 5,726,115 A | 3/1998 | Horton et al. | 502/152 |
| 5,830,629 A | 11/1998 | Vizard et al. | 430/523 |
| 5,852,145 A | 12/1998 | McLain et al. | 526/133 |
| 5,888,647 A | 3/1999 | Yamane | 428/338 |
| 5,905,014 A | 5/1999 | Van de Bergh | 430/139 |
| 5,955,555 A | 9/1999 | Bennett | 526/133 |
| 6,002,034 A | 12/1999 | McLain et al. | 556/34 |
| 6,063,881 A | 5/2000 | Bennett | 526/161 |
| 6,103,946 A | 8/2000 | Brookhart et al. | 585/523 |
| 6,150,482 A | 11/2000 | Brookhart et al. | 526/161 |
| 6,214,761 B1 | 4/2001 | Bennett | 502/117 |
| 6,232,259 B1 | 5/2001 | Ittel et al. | 502/155 |
| 6,265,500 B1 | 7/2001 | Debras | 526/65 |
| 6,310,153 B2 | 10/2001 | Ittel et al. | 526/172 |
| 6,395,668 B1 | 5/2002 | van Baar et al. | 502/123 |
| 6,407,188 B1 | 6/2002 | Guan et al. | 526/113 |
| 6,414,098 B1 | 7/2002 | Engehausen et al. | 526/161 |
| 6,417,305 B2 | 7/2002 | Bennett | 526/161 |
| 6,417,364 B1 | 7/2002 | Lenges | 546/12 |
| 6,423,848 B2 | 7/2002 | Bennett | 546/329 |
| 6,432,862 B1 | 8/2002 | Bennett | 502/117 |
| 6,441,117 B1 | 8/2002 | Cameron | 526/352 |
| 6,451,939 B1 | 9/2002 | Britovsek et al. | 526/161 |
| 6,455,660 B1 | 9/2002 | Clutton et al. | 526/352 |
| 6,458,739 B1 | 10/2002 | Kimberley et al. | 502/155 |

(Continued)

FOREIGN PATENT DOCUMENTS

EP    0308728    3/1989

(Continued)

OTHER PUBLICATIONS

Lions et al, "Tridentate Chelate Compounds. I." J. Am. Chem. Soc. (1957), vol. 79, 2733-38.*

(Continued)

*Primary Examiner*—Kamal A. Saeed
*Assistant Examiner*—Janet L. Coppins
(74) *Attorney, Agent, or Firm*—Donald F. Haas

(57) ABSTRACT

Mixed bis-imine pyridine ligands of formula (I), wherein $Z_1$, which is different from $Z_2$, is an optionally substituted aryl group; and $Z_2$ comprises an optionally substituted heterohydrocarbyl moiety, or an optionally substituted aryl group in combination with a metal, said optionally substituted aryl group being π-co-ordinated to the metal;

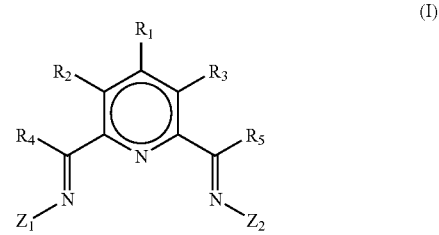

(I)

mixed bis-imine pyridine complexes comprising a ligand of formula (I); mixed ionic bis-imine pyridine complexes comprising a ligand of formula (I); and processes for the production of alpha olefins from ethylene, using said complexes.

21 Claims, 2 Drawing Sheets

U.S. PATENT DOCUMENTS

| | | | |
|---|---|---|---|
| 6,458,905 B1 | 10/2002 | Schmidt et al. | 526/172 |
| 6,461,994 B1 | 10/2002 | Gibson et al. | 502/155 |
| 6,462,152 B1 | 10/2002 | Berardi et al. | 526/75 |
| 6,462,155 B1 | 10/2002 | Okuda | 526/161 |
| 6,465,386 B1 | 10/2002 | Maddox et al. | 502/155 |
| 6,472,341 B1 | 10/2002 | Kimberley et al. | 502/155 |
| 6,479,601 B1 | 11/2002 | Kerns et al. | 526/161 |
| 6,489,497 B1 | 12/2002 | Brookhart, III et al. | 556/138 |
| 6,521,329 B2 | 2/2003 | Aylward et al. | 428/212 |
| 6,534,691 B2 | 3/2003 | Culver et al. | 585/527 |
| 6,545,108 B1 | 4/2003 | Moody et al. | 526/161 |
| 6,548,672 B1 | 4/2003 | Gibson et al. | 546/12 |
| 6,555,723 B2 | 4/2003 | Schiffino | 585/521 |
| 6,559,091 B1 | 5/2003 | Moody et al. | 502/167 |
| 6,559,252 B1 | 5/2003 | Horton et al. | 526/160 |
| 6,583,237 B1 | 6/2003 | Imuta et al. | 526/89 |
| 6,605,677 B2 | 8/2003 | Lavoie et al. | 526/161 |
| 6,677,267 B2 | 1/2004 | Berardi et al. | 502/155 |
| 6,683,141 B1 | 1/2004 | Gibson et al. | 526/161 |
| 6,683,187 B2 | 1/2004 | De Boer et al. | 546/345 |
| 6,706,891 B2 | 3/2004 | Ponasik | 548/523 |
| 6,710,006 B2 | 3/2004 | De Boer et al. | 502/155 |
| 6,740,715 B2 | 5/2004 | Brookhart, III et al. | 526/161 |
| 6,825,297 B1 | 11/2004 | Devore et al. | 526/172 |
| 6,838,540 B2 | 1/2005 | Mitani et al. | 526/348 |
| 7,049,442 B2 | 5/2006 | De Boer et al. | 546/268.1 |
| 7,053,020 B2 * | 5/2006 | De Boer et al. | 502/155 |
| 7,179,871 B2 | 2/2007 | De Boer et al. | 526/161 |
| 2001/0000519 A1 | 4/2001 | Bennett | 526/329 |
| 2001/0016634 A1 | 8/2001 | Ittel et al. | 526/172 |
| 2002/0013431 A1 | 1/2002 | Bennett | 526/90 |
| 2002/0016425 A1 | 2/2002 | De Boer et al. | 526/172 |
| 2002/0016521 A1 | 2/2002 | Culver et al. | 585/527 |
| 2002/0019575 A1 | 2/2002 | Schiffino | 585/521 |
| 2002/0028941 A1 | 3/2002 | De Boer et al. | 546/167 |
| 2002/0035031 A1 | 3/2002 | Berardi et al. | 502/171 |
| 2002/0128409 A1 | 9/2002 | De Boer et al. | |
| 2003/0036615 A1 | 2/2003 | Brookhart, III et al. | 526/161 |
| 2003/0045752 A1 | 3/2003 | De Boer et al. | 562/545 |
| 2003/0050494 A1 | 3/2003 | Brookhart, III et al. | 556/138 |
| 2003/0119921 A1 | 6/2003 | De Boer et al. | 518/715 |
| 2003/0125195 A1 | 7/2003 | Britovsek et al. | 502/117 |
| 2003/0144514 A1 | 7/2003 | De Boer et al. | |
| 2003/0195110 A1 | 10/2003 | Moody et al. | 502/150 |
| 2003/0225228 A1 | 12/2003 | Moody et al. | 526/172 |
| 2004/0116758 A1 | 6/2004 | De Boer et al. | |
| 2005/0014983 A1 | 1/2005 | De Boer et al. | 585/511 |
| 2005/0159601 A1 | 7/2005 | De Boer et al. | 546/2 |

FOREIGN PATENT DOCUMENTS

| | | |
|---|---|---|
| EP | 1125928 | 8/2001 |
| EP | 1125987 A2 | 8/2001 |
| EP | 0927201 B1 | 4/2004 |
| JP | 04325504 | 11/1992 |
| RU | 418462 | 9/1974 |
| WO | 98/27124 | 6/1998 |
| WO | 99/02472 | 1/1999 |
| WO | WO 99/12981 | 3/1999 |
| WO | WO9951550 | 10/1999 |
| WO | 99/62967 | 12/1999 |
| WO | WO 00/50470 | 8/2000 |
| WO | WO 01/36379 A1 | 5/2001 |
| WO | WO 02/28805 A2 | 4/2002 |

OTHER PUBLICATIONS

U.S. Appl. No. 10/739,715, filed Dec. 18, 2003, De Boer et al.

D. Vogt, *Oligomerisation of ethylene to higher a-olefins* in *Applied Homogeneous Catalysis with Organometallic Compounds* Ed. B. Cornils, W.A. Herrmann vol. 1, Ch. 2.3.1.3, p. 245, VCH 1996.

D. van Leusen and B. Hessen, Organometallics, 2001, 20, pp. 224-226.

Chemical Abstracts, vol. 134, Columbus, Ohio, US; Abstract No. 231149, Radecka-Paryzek, W. et al., "Metal-ion-directed synthesis of homo- and heteronuclear dimetallic Schiff base podates," Pol. J. Chem. 2001, 75(1), pp. 35-42.

Office Action dated Nov. 29, 2004 regarding U.S. Appl. No. 10/208,535, filed Jul. 30, 2002.

Amendment in response to the Office Action of Nov. 29, 2004 regarding U.S. Appl. No. 10/208,535, filed Jul. 30, 2002.

Lions, Francis et al. "Tridentals Chelate Compounds. I" J. Am. Chem. Soc. (1957), vol. 79, 2733-38.

Figgins, Paul et al. "Complexes of Iron (II), Co(II); and N(II) with Biacetyl-bis-methylimine, 2-pyridinal-methylimine and 2,6-pyridindial-bis-methylimine," J.Am. Chem. Soc. (1960), vol. 82, 820-824.

Office Action of Mar. 23, 2005 in patent application TS1266 (U.S. Appl. No. 10/668,592, filed Sep. 23, 2003).

Response to Office Action of Mar. 23, 2005 in patent application TS1266 (U.S. Appl. No. 10/668,592, filed Sep. 23, 2003) dated Jun. 10, 2005.

George J. P. Britovsek et al., "Iron-Catalyzed Polyethylene Chain Growth on Zinc: Linear α-Olefins with a Poisson Distribution," Angew. Chem. Int. Ed. 2002, 41, No. 3, pp. 489-491.

International Preliminary Examination Report for PCT/EP 03/10708 of Jan. 3, 2005.

U.S. Appl. No. 11/080,170, filed Mar. 15, 2005, De Boer et al.

"Iron-Based Catalysts With Exceptionally High Activities and Selectivities for Oligomerization of Ethylene to Linear α-Olefins," B. L. Small and M. Brookhard disclosed in *J. Am. Chem. Soc.* 1998, 120, pp. 7143-7144.

"Oligomerisation of Ethylene by Bis(Imino)Pyridyliron and—Cobalt Complexes," by G. J. P. Britovsek, S. Mastroianni, G. A. Solan, S. P. D. Baugh, C. Redshaw, V. C. Gibson, A. J. P. White, D. J. Williams, and M. R. J. Elsegood, as disclosed in *Chem. Eur. J.* 2000, 6, pp. 2221-2231.

Olefin Polymerization with [{bis(imino)pyridyl}CO$^{11}$Cl$_2$]: Generation of the Active Species Involves CO$^{1}$**, by T. Martijn Kooistra et al., Angewandte Chemie. International Edition, WILEY-VCH, Weinheim, DE, vol. 40, No. 24, Dec. 17, 2001, pp. 4719-4722.

"The Nature of the Active Species in Bis(imino)pyridyl Cobalt Ethylene Polymerisation Catalysts," by Vernon C. Gibson, et al., Chemical Communications-Chemcom, Royal Society of Chemistry, GB, No. 21, 2001, pp. 2252-2253.

"Novel, Highly Active Iron and Cobalt Catalysts for Olefin Polymerization," by Allison M. A. Bennett, Chemtech, Jul. 1999, pp. 24-28.

"Late Metal Catalysts for Ethylene Homo- and Copolymerization," by Steven D. Ittel et al., Chemical Reviews, American Chemical Society, Easton, US, vol. 100, No. 4, 2000, pp. 1169-1203.

"Novel Olefin Polymerization Catalysts Based on Iron and Cobalt," by George J. P. Britovsek et al., Chemical Communications-Chemcom, Roayl Society of Chemistry, GB, No. 7, 1998, pp. 849-850.

"Polymerization of Propylene by a New Generation of Iron Catalysts: Mechanisms of Chain Initiation, Propagation, and Termination," by Brooke L. Small and Maurice Brookhart, Macromolecules, vol. 32, No. 7, 1999, pp. 2120-2130.

"Metal-Ion-Directed Synthesis of Homo- and Heteronuclear Dimetallic Schiff Base Podates," by W. Radecka-Paryzek, M. T. Kaczmarek, and E. Luks, Polish J. Chem., 75, (2001) pp. 35-42.

"1, 1-Diisocyanoferrocene and a Convenient Synthesis of Ferrocenylamine," by Daan van Leusen and Bart Hessen, Organometallics, 2001, pp. 224-226.

International Preliminary Examination Report on Patentability for PCT/US2004/051365 of Aug. 29, 2005.

* cited by examiner

LIGANDS AND CATALYST SYSTEMS THEREOF FOR ETHYLENE OLIGOMERISATION TO LINEAR ALPHA OLEFINS

REFERENCE TO RELATED APPLICATIONS

This application is a divisional of U.S. Ser. No. 10/208,535, filed Jul. 30, 2002 now U.S. Pat. No. 7,049,442, the disclosure of which is herein incorporated by reference.

FIELD OF THE INVENTION

The present invention relates to ligands, various catalyst precursors and catalyst systems derived from these ligands for ethylene oligomerisation to linear alpha olefins in high yield and very high selectivity, and a process for preparing said linear alpha olefins.

BACKGROUND OF THE INVENTION

Various processes are known for the production of higher linear alpha olefins (for example D. Vogt, *Oligomerisation of ethylene to higher α-olefins* in *Applied Homogeneous Catalysis with Organometallic Compounds* Ed. B. Cornils, W. A. Herrmann Vol. 1, Ch. 2.3.1.3, page 245, VCH 1996). These commercial processes afford either a Poisson or Schulz-Flory oligomer product distribution.

In order to obtain a Poisson distribution, no chain termination must take place during oligomerisation.

However, in contrast, in a Schulz-Flory process, chain termination does occur and is independent from chain length. The Ni-catalysed ethylene oligomerisation step of the Shell Higher Olefins Process (SHOP) is a typical example of a Schulz-Flory process.

In a Schulz-Flory process, a wide range of oligomers are typically made in which the fraction of each olefin can be determined by calculation on the basis of the so-called K-factor. The K-factor, which is indicative of the relative proportions of the product olefins, is the molar ratio of $[C_{n+2}]/[C_n]$ calculated from the slope of the graph of log $[C_n$ mol %] versus n, where n is the number of carbon atoms in a particular product olefin. The K-factor is by definition the same for each n. By ligand variation and adjustment of reaction parameters, the K-factor can be adjusted to higher or lower values. In this way, the process can be operated to produce a product slate with an optimised economic benefit.

Since demand for the $C_6$-$C_{18}$ fraction is much higher than for the $C_{>20}$ fraction, processes are geared to produce the lower carbon number olefins. However, the formation of the higher carbon number olefins is inevitable, and, without further processing, the formation of these products is detrimental to the profitability of the process. To reduce the negative impact of the higher carbon number olefins and of the low value $C_4$ fraction, additional technology has been developed to reprocess these streams and convert them into more valuable chemicals such as internal $C_6$-$C_{18}$ olefins, as is practised in the Shell Higher Olefins Process.

However, this technology is expensive both from an investment and operational point of view and consequently adds additional cost. Therefore considerable effort is directed to keep the production of the higher carbon numbered olefins to the absolute minimum, i.e. not more than inherently associated with the Schulz-Flory K-factor.

WO-A-99/12981 describes catalyst systems for the polymerisation of 1-olefins, in particular ethylene, which contain nitrogen-containing transition metal compounds comprising a skeletal unit of formula (B),

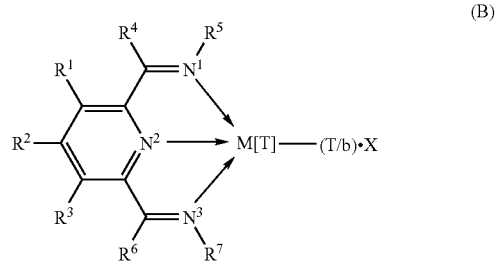

(B)

wherein M is Fe [II], Fe [III], Ru [II], Ru [III] or Ru [IV]; x represents an atom or group covalently or ionically bonded to the transition metal M; T is the oxidation state of the transition metal M and b is the valency of the atom or group X; $R^1$, $R^2$, $R^3$, $R^4$ and $R^6$ are independently selected from hydrogen, halogen, hydrocarbyl, substituted hydrocarbyl, heterohydrocarbyl or substituted heterohydrocarbyl, $R^5$ and $R^7$ are independently selected from hydrogen, halogen, hydrocarbyl, substituted hydrocarbyl, heterohydrocarbyl or substituted heterohydrocarbyl.

WO-A-00/50470 discloses catalyst compositions that it is said may be used in the polymerisation or oligomerisation of olefins.

Said catalyst compositions comprise a metal complex ligated by a monodentate, bidentate, tridentate or tetradentate ligand, wherein at least one of the donor atoms of the ligand is a nitrogen atom substituted by a 1-pyrrolyl or substituted 1-pyrrolyl group; wherein the remaining donor atoms of the ligand are selected from the group consisting of C, N, P, As, O, S and Se; and wherein said metal in said metal complex is selected from the group consisting of Se, Ta, Ti, Zr, Hf, V, Nb, Cr, Mo, W, Mn, Re, Fe, Ru, Os, Co, Rn, Ir, Ni, Cu, Pd, Pt, Al and Ga.

Ligand, h1, is said to be one of a number of neutral tridentate ligands that may be used in preferred catalyst compositions according to WO-A-00/50470:—

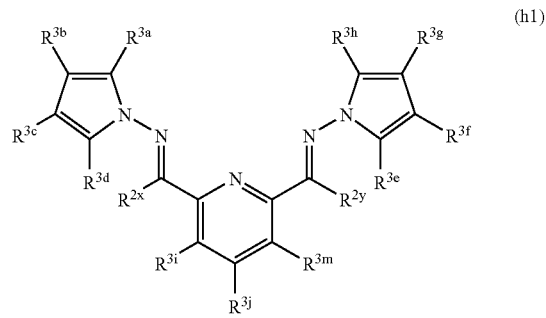

(h1)

In particular, a number of symmetrical bis-pyrrolyl imine ligands, h16-h17, h19-h25, h28, h30 and h32 are specifically disclosed. In addition, h29, h31 and h33 are mixed bis-pyrrolyl imine ligands.

Examples 59, 60 and 62 of WO-A-00/50470 demonstrate the polymerisation of ethylene in the presence of an iron-based catalyst composition comprising symmetrical bis-pyrrolyl imine ligand h16.

Similarly, Example 74 concerns the polymerisation of ethylene in the presence of an iron-based catalyst composition comprising symmetrical bis-pyrrolyl imine ligand h17.

Further examples of ethylene polymerisation in WO-A-00/50470, employing some of the afore-mentioned ligands in iron-based catalyst compositions, include Examples 99-125; 128, 131, 133 and 135 therein.

As exemplified in Example 4 herein, the lower homologue of ligand h16 of WO-A-00/50470, that is to say, ligand (11), gives rise to an iron-based bis-pyrrolyl imine catalyst composition which gives little, if any, ethylene conversion.

SUMMARY OF THE INVENTION

Accordingly there is provided a mixed bis-imine pyridine ligand of formula (I):

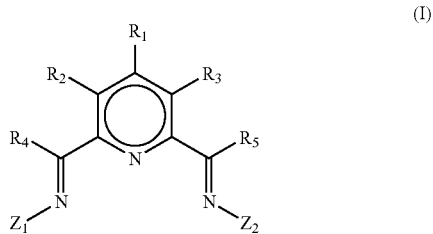

(I)

wherein $R_1$-$R_5$ are each, independently, hydrogen, optionally substituted hydrocarbyl, an inert functional group, or any two of $R_1$-$R_3$ vicinal to one another taken together may form a ring; $Z_1$, which is different from $Z_2$, is an optionally substituted aryl group; and $Z_2$ is a heterohydrocarbyl group containing an optionally substituted heterohydrocarbyl moiety, or an optionally substituted aryl group in combination with a metal, said optionally substituted aryl group being π-co-ordinated to the metal. In one embodiment there is provided the ligand of claim 1 wherein a bis-imine pyridine ligand of formula (II):

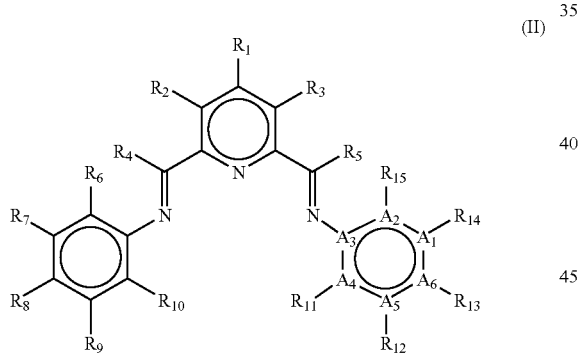

(II)

wherein $A_1$-$A_6$ are each, independently, carbon, nitrogen, oxygen, or sulphur; the atom group

may be optionally absent such that $A_1$ is directly bonded to $A_5$; and $R_1$-$R_{12}$, $R_{14}$-$R_{15}$ and, if present, $R_{13}$, are each, independently, hydrogen, optionally substituted hydrocarbyl, an inert functional group, or any two of $R_1$-$R_{15}$ vicinal to one another taken together may form a ring; with the proviso that when $A_1$-$A_5$, and $A_6$ if present, are all carbon, said atoms constitute the cyclopentadienyl or aryl part of a π-co-ordinated metal. In another embodiment, there is provided mixed bis-imine pyridine complexes comprising such ligands. In a further embodiment, a process for the production of alpha olefins from ethylene using such complexes are provided.

DETAILED DESCRIPTION OF THE INVENTION

Figure 1:
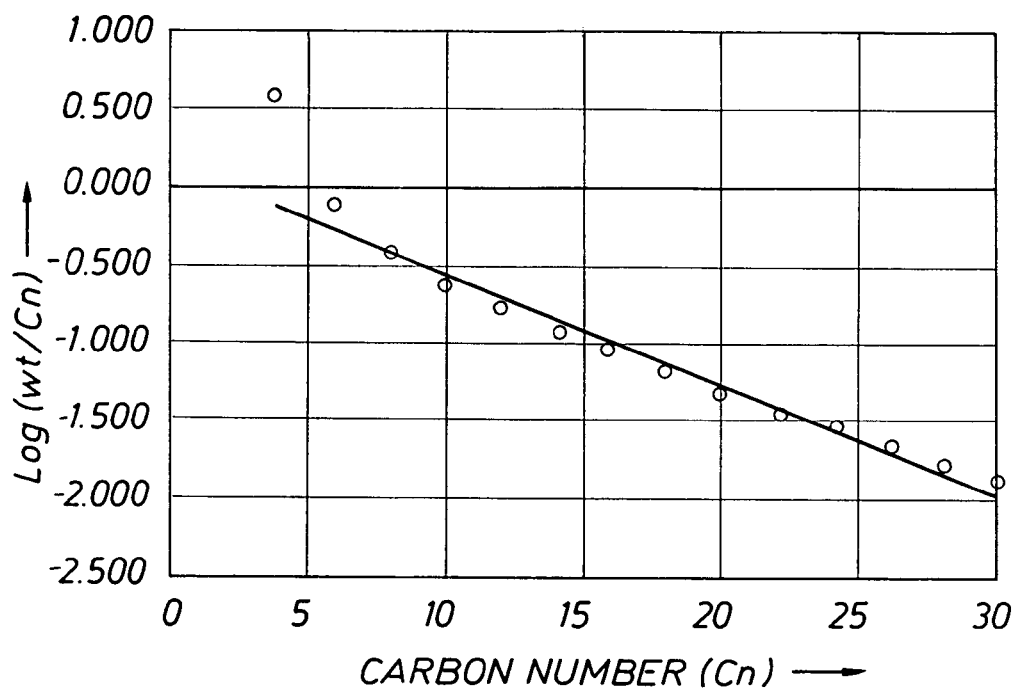
FIG. 1 is a regression analysis of Example 2.

There has now been surprisingly found a novel class of catalysts which are highly active in the oligomerisation of olefins, especially ethylene, and which produce linear alpha olefins in the $C_{6-30}$ range, said linear alpha olefins being of high purity.

Furthermore, some of the catalysts of the present invention give rise to a Schulz-Flory product distribution.

The present invention provides a mixed bis-imine pyridine ligand of formula (I), wherein $R_1$-$R_5$ are each, independently, hydrogen, optionally substituted hydrocarbyl, an inert functional group, or any two of $R_1$-$R_3$ vicinal to one another taken together may form a ring; $Z_1$, which is different from $Z_2$, is an optionally substituted aryl group; and $Z_2$ comprises an optionally substituted heterohydrocarbyl moiety, or an optionally substituted aryl group in combination with a metal, said optionally substituted aryl group being π-co-ordinated to the metal.

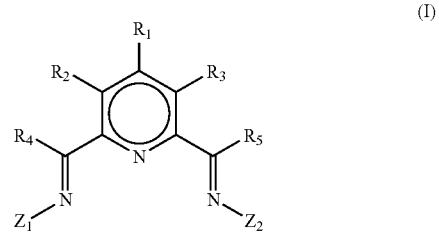

(I)

The present invention further provides a mixed bis-imine pyridine $MX_n$ complex comprising a mixed bis-imine pyridine ligand of formula (I), wherein M is a metal atom selected from Fe or Co, n is 2 or 3, and X is halide, optionally substituted hydrocarbyl, alkoxide, amide, or hydride.

In a further aspect, the present invention provides a process for the production of alpha-olefins, which comprises contacting one or more $MX_n$ complexes of the present invention with ethylene and a second compound which is capable of transferring an optionally substituted hydrocarbyl or hydride group to a metal atom M selected from Fe or Co, and which is also capable of abstracting an $X^-$ group from said metal atom, at a temperature in the range of −100° C. to +300° C.

In a still further aspect, the present invention provides a process for the production of alpha-olefins, which comprises contacting one or more $MX_n$ complexes of the present invention with ethylene and a second compound which is capable of transferring an optionally substituted hydrocarbyl or hydride group to a metal atom M selected from Fe or Co, and a third compound which is capable of abstracting an $X^-$ group from said metal atom, at a temperature in the range of −100° C. to +300° C.

The present invention further provides a mixed [bis-imine pyridine $MY_p.L_n^+][NC^-]_q$ ("ionic") complex comprising a ligand of formula (I), wherein Y is a ligand which may insert an olefin; M is a metal atom selected from Fe or Co, $NC^-$ is a non-coordinating anion and p+q is 2 or 3, matching the formal oxidation of said metal atom; L is a neutral Lewis donor molecule and n=0, 1, or 2.

The present invention further provides a process for the production of alpha-olefins, comprising contacting one or more mixed [bis-imine pyridine $MY_p.L_n^+][NC^-]_q$ complexes of the present invention with ethylene at a temperature in the range of −100° C. to +300° C.

In the present invention certain terms are used as follows:

The term "mixed" denotes that the imine moieties, $Z_1$ and $Z_2$, are each different.

The term "aryl" refers to an aromatic cyclic hydrocarbon monoradical. Examples include phenyl, naphthyl, anthracenyl, phenanthracenyl, and the like and substituted derivatives thereof.

The term "optionally substituted aryl group in combination with a metal, said optionally substituted aryl group being π-co-ordinated to the metal" includes metallocene moieties and sandwich and metal-arene complexes. Thus, it will be appreciated by the person skilled in the art, that, optionally, the metal may be additionally π-co-ordinated to a further optionally substituted aryl group, which may be different to the optionally substituted aryl group in $Z_2$ which is directly bonded to the imine nitrogen atom and/or co-ordinated to other ligands commonly known in the art. It will further be appreciated that the optionally substituted aryl group in $Z_2$ which is directly bonded to the imine nitrogen atom and which is also π-co-ordinated to the metal, may comprise one or more heteroatoms in the ring, i.e., such that said optionally substituted aryl group is an optionally substituted heteroaryl group. Similarly, the further optionally substituted aryl group that the metal may additionally be π-co-ordinated to, may comprise one or more heteroatoms in the ring. Said metal atom may conveniently be iron, cobalt, nickel, chromium, titanium and vanadium. Examples of such moieties include the radical derived from ferrocene, cobaltocene, nickelocene, chromocene, titanocene, vanadocene, bis-π-arene vanadium complex, mono-π-arene chromium tricarbonyl complex and similar heteroarene metal complexes, i.e. bis- or mono-π-thiene or pyrrole iron or chromium complexes.

The term "heterohydrocarbyl" refers to a hydrocarbyl group, additionally containing one or more heteroatoms. Said heteroatoms are preferably bonded to at least two carbons in the heterohydrocarbyl group.

Said heterohydrocarbyl group may be an optionally substituted aromatic heterocyclic moiety; an optionally substituted polyaromatic heterocyclic moiety; an optionally substituted aliphatic heterocyclic moiety; or an optionally substituted aliphatic heterohydrocarbyl moiety.

Examples of heterohydrocarbyl groups include 1-pyrrolyl, 2-pyrrolyl, 3-pyrrolyl, furyl, thienyl, indenyl, imidazolyl, triazolyl, oxazolyl, isoxazolyl, carbazolyl, thiazolyl, benzothiazolyl, thiadiazolyl, pyrimidinyl, pyridyl, pyridazinyl, and the like and substituted derivatives thereof.

Hydrocarbyl group: a group containing only carbon and hydrogen. Unless otherwise stated, the number of carbon atoms is preferably between 1 and 30.

In the present invention, the phrase "optionally substituted hydrocarbyl" is used to describe hydrocarbyl groups optionally containing one or more "inert" heteroatom-containing functional groups. By "inert" is meant that the functional groups do not interfere to any substantial degree with the oligomerisation process. Non-limiting examples of such inert groups are fluoride, chloride, silanes, stannanes, ethers and amines with adequate steric shielding, all well-known to those skilled in the art.

Inert functional group: a group other than optionally substituted hydrocarbyl which is inert under the process conditions. By "inert" is meant that the functional group does not interfere to any substantial degree with the oligomerisation process. Examples of inert functional groups include halide, ethers, and amines, in particular tertiary amines.

Primary carbon atom group: a $-CH_2-R$ group wherein R may be hydrogen, optionally substituted hydrocarbyl, inert functional group. Examples of primary carbon atom groups include $-CH_3$, $-C_2H_5$, $-CH_2Cl$, $-CH_2OCH_3$, $-CH_2N(C_2H_5)_2$, $-CH_2Ph$.

Secondary carbon atom group: a $-CH-R_2$ group wherein R may be optionally substituted hydrocarbyl, inert functional group. Examples of secondary carbon atom groups include $-CH(CH_3)_2$, $-CHCl_2$, $-CHPh_2$, $-CH=CH_2$, cyclohexyl.

Tertiary carbon atom group: a $-C-R_3$ group wherein R may be optionally substituted hydrocarbyl, inert functional group. Examples of tertiary carbon atom groups include $-C(CH_3)_3$, $-CCl_3$, $-C≡CPh$, 1-Adamantyl, $-C(CH_3)_2(OCH_3)$.

By a "ligand which may insert an olefin" is meant a ligand which is coordinated to a metal ion into which bond an ethylene molecule may be inserted to initiate or propagate an oligomerisation reaction. In mixed [aryl-, (hetero)aryl-imine pyridine $MY_p.L_n^+][NC^-]_q$ complexes according to the present invention, Y may be hydride, alkyl or any other anionic ligand which may insert an olefin.

By "non-coordinating anion" is meant an anion which does not substantially coordinate to the metal atom M.

Non-coordinating anions ($NC^-$) that may be suitably employed include bulky anions such as tetrakis[3,5-bis(trifluoromethyl)phenyl]borate ($BAF^-$), $(C_6F_5)_4B^-$, and anions of alkylaluminium compounds including $R_3AlX^-$, $R_2AlClX^-$, $RAlCl_2X^-$, and "$RAlOX^-$", wherein R is hydrogen, optionally substituted hydrocarbyl or an inert functional group, and X is halide, alkoxide or oxygen.

It will be appreciated by those skilled in the art that within the boundary conditions herein before described, substituents $R_1$-$R_{15}$ may be readily selected to optimise the performance of the catalysts system and its economical application.

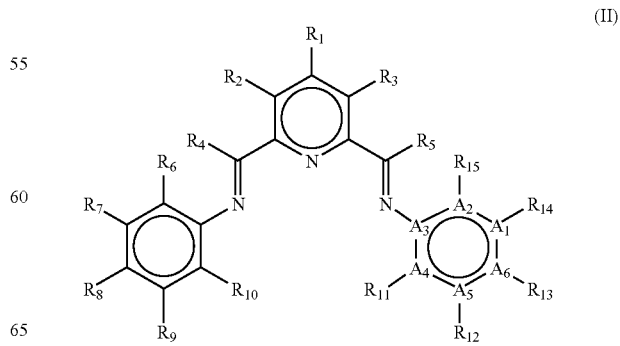

(II)

In a preferred embodiment, the present invention provides mixed bis-imine pyridine ligands of formula (II) wherein $A_1$-$A_6$ are each, independently, carbon, nitrogen, oxygen, or sulphur; the atom group

may be optionally absent such that $A_1$ is directly bonded to $A_5$; and $R_1$-$R_{12}$, $R_{14}$-$R_{15}$ and, if present, $R_{13}$, are each, independently, hydrogen, optionally substituted hydrocarbyl, an inert functional group, or any two of $R_1$-$R_{15}$ vicinal to one another taken together may form a ring; with the proviso that when $A_1$-$A_5$, and $A_6$ if present, are all carbon, said atoms constitute the cyclopentadienyl or aryl part of a π-co-ordinated metal.

In a preferred embodiment of the present invention, in formula (II), $R_1$-$R_3$, $R_7$-$R_9$, $R_{12}$, $R_{14}$ and, if present, $R_{13}$, are each, independently, hydrogen, optionally substituted hydrocarbyl, an inert functional group, or any two of $R_1$-$R_3$, $R_7$-$R_9$, $R_{12}$-$R_{14}$ vicinal to one another taken together may form a ring; and a) $R_6$ is an inert functional group or an optionally substituted hydrocarbyl, and $R_{10}$, $R_{11}$, and $R_{15}$ are, independently, hydrogen or halide; or b) $R_{11}$ is an inert functional group or an optionally substituted hydrocarbyl, and $R_6$, $R_{10}$, and $R_{15}$ are, independently, hydrogen or halide; or c) $R_6$ and $R_{10}$ are each, independently, inert functional group or a primary or secondary carbon atom group, provided that $R_6$ and $R_{10}$ are not both a secondary carbon atom group and $R_{11}$ and $R_{15}$ are, independently, hydrogen or halide; or d) $R_{11}$ and $R_{15}$ are each, independently, inert functional group or a primary or secondary carbon atom group, provided that $R_{11}$ and $R_{15}$ are not both a secondary carbon atom group and $R_6$ and $R_{10}$ are, independently, hydrogen or halide; or e) $R_6$ is taken together with $R_7$ to form a ring, $R_{10}$ is a primary carbon atom group, an inert functional group, or hydrogen and $R_{11}$ and $R_{15}$ are, independently, hydrogen or halide; or f) $R_{11}$ is taken together with $R_{12}$ to form a ring, $R_{15}$ is a primary carbon atom group, an inert functional group, or hydrogen and $R_6$ and $R_{10}$ are, independently, hydrogen or halide; or g) $R_6$ and $R_{10}$ are taken together with $R_7$ and $R_9$, respectively, to form rings and $R_{11}$ and $R_{15}$ are, independently, hydrogen or halide; or h) $R_{11}$ and $R_{15}$ are taken together with $R_{12}$ and $R_{14}$, respectively, to form rings and $R_6$ and $R_{10}$ are, independently, hydrogen or halide.

Substituents $R_{1-15}$, if present, may independently be linked together and form cyclic structures. Examples of such structures include the linking of, for example, $R_6$ with $R_7$, to form the basic naphthyl skeleton or a tetrahydronaphthyl unit.

Furthermore it will be readily appreciated by any person who has mastered the basic principles of homogeneous catalysis that substituent variations of $R_{1-5}$, $R_{7-9}$, and $R_{12-14}$, if present, may be selected so as to enhance other desirable properties of catalyst precursors and catalyst systems such as solubility in non-polar solvents or extending the range of suitable starting materials in their syntheses.

Preferred embodiments of this invention are ligands according to (I) and derivatives thereof, in which the following R and Z groups appear:

$R_1$-$R_3$ are hydrogen; and/or $Z_1$ is optionally substituted phenyl and $Z_2$ is optionally substituted ferrocenyl or optionally substituted 1-pyrrolyl.

Preferred embodiments of this invention are ligands according to (II) and derivatives thereof, in which the following R groups appear:

$R_1$-$R_3$ are hydrogen; and/or $R_4$ and $R_5$ are methyl, hydrogen or phenyl, preferably methyl; and/or

is absent and $A_1$-$A_5$ are carbon atoms, thereby constituting the cyclopentadienylide part of a ferrocenyl moiety; or $A_3$ is a nitrogen atom,

is absent and $A_1$, $A_2$, $A_4$, $A_5$ are carbon atoms, thereby constituting a pyrrolyl ring; and/or Combinations of ortho-substituents in which $R_6$ is methyl, ethyl, iso-propyl, phenyl, tertiary-butyl, or linked to $R_7$ to form a naphthyl skeleton; $R_{10}$ is hydrogen, fluoride, or chloride; $R_{11}$ and $R_{15}$ are, independently, hydrogen, fluoride or chloride and/or Combinations of ortho-substituents in which $R_6$ and $R_{10}$ are, independently, methyl, ethyl, or linked to $R_7$ and $R_9$ respectively, to form an anthracene skeleton, preferably methyl; $R_{11}$ and $R_{15}$ are, independently, hydrogen, fluoride or chloride.

It is particularly preferred that $R_{11}$ and $R_{15}$ are, independently, hydrogen or fluoride.

In a preferred embodiment, a ligand of formula (II) is provided, wherein $R_1$-$R_3$ are hydrogen; $A_6$-$R_{13}$ is absent and $A_1$-$A_5$ are carbon atoms, thereby constituting the cyclopentadienylide part of a ferrocenyl moiety; $R_4$, $R_5$, $R_6$, $R_8$ and $R_{10}$ are methyl; $R_7$, $R_9$, $R_{11}$, $R_{12}$, $R_{14}$ and $R_{15}$ are hydrogen.

In another preferred embodiment, a ligand of formula (II) is provided, wherein $R_1$-$R_3$ are hydrogen; $A_6$-$R_{13}$ is absent and $A_1$-$A_5$ are carbon atoms, thereby constituting the cyclopentadienylide part of a ferrocenyl moiety; $R_4$ and $R_5$ are methyl; $R_6$ and $R_{10}$ are ethyl; $R_7$, $R_8$, $R_9$, $R_{11}$, $R_{12}$, $R_{14}$ and $R_{15}$ are hydrogen.

In another preferred embodiment, a ligand of formula (II) is provided, wherein $R_1$-$R_3$ are hydrogen; $A_3$ is a nitrogen atom, $A_6$-$R_{13}$ is absent and $A_1$, $A_2$, $A_4$, $A_5$ are carbon atoms, thereby constituting 1-pyrrolyl ring; $R_4$ and $R_5$ are methyl; $R_6$ and $R_{10}$ are ethyl; $R_7$, $R_8$, $R_9$, $R_{11}$, $R_{12}$, $R_{14}$ and $R_{15}$ are hydrogen.

In a particularly preferred embodiment, a ligand of formula (II) is provided, wherein $R_1$-$R_3$ are hydrogen; $A_3$ is a nitrogen atom, $A_6$-$R_{13}$ is absent and $A_1$, $A_2$, $A_4$ and $A_5$ are carbon atoms, thereby constituting 1-pyrrolyl ring; $R_4$, $R_5$, $R_6$, $R_8$ and $R_{10}$ are methyl; $R_7$, $R_9$, $R_{11}$, $R_{12}$, $R_{14}$ and $R_{15}$ are hydrogen.

In the derived mixed bis-imine pyridine $MX_n$ complex, X may conveniently be halide, preferably chloride.

In a preferred embodiment of the mixed bis-imine pyridine $MX_n$ complex, metal atom M is Fe and n is 2. In another preferred embodiment, metal atom M is Fe and n is 3.

Compounds which are capable of transferring an optionally substituted hydrocarbyl or hydride group to metal atom M, and which are also capable of abstracting an $X^-$ group from metal atom M include alkylaluminium compounds such as alkylaluminoxane and alkylaluminium halides. A preferred compound is methylaluminoxane.

Compounds which are capable of transferring an optionally substituted hydrocarbyl or hydride group to metal atom M include alkylaluminium compounds including alkyl aluminoxanes, alkyl lithium compounds, Grignards, alkyl tin and alkyl zinc compounds.

Compounds which are capable of abstracting an $X^-$ group from metal atom M include strong neutral Lewis acids such as $SbF_5$, $BF_3$ and $Ar_3B$, wherein Ar is a strong electron-withdrawing aryl group such as $C_6F_5$ or $3,5\text{-}(CF_3)_2C_6H_3$.

A neutral Lewis donor molecule is a compound which may suitably act as a Lewis base, such as ethers, amines, sulphides and organic nitriles.

The use of donor molecules (Lewis bases) such as triethylamine or 2,6-di-tert-butylpyridine, and/or acceptor molecules (Lewis acids) such as diethyl zinc, may have a positive influence on the selectivity of the ethylene oligomerisation process to 1-olefins.

Furthermore, Lewis acids such as tri-isobutylaluminium (TIBA) may enhance the continuous operation of the Fe- or Co-catalysed ethylene oligomerisation by enabling the preparation of stable and clear catalyst precursor solutions, in contrast to MAO activated and solubilised catalyst solutions, which may become turbid upon standing.

In the mixed $[\text{bis-imine pyridine } MY_p.L_n^+][NC^-]_q$ complex according to the present invention, L may be a neutral Lewis donor molecule capable of being displaced by ethylene, or a vacant coordination site.

In the mixed $[\text{bis-imine pyridine } MY_p.L_n^+][NC^-]_q$ complex according to the present invention, metal atom M is preferably Fe and the formal oxidation state of said metal atom may be 2 or 3.

The catalyst system may be formed by mixing together the complex and optional additional compounds, preferably in a solvent such as toluene or isooctane.

Such a quantity of the catalyst system is usually employed in the oligomerisation reaction mixture as to contain from $10^{-4}$ to $10^{-9}$ gram atom, more preferably $10^{-6}$ to $10^{-7}$ gram atom, of metal atom M, in particular of Fe [II] or [III] metal per mole of ethylene to be reacted.

The oligomerisation reaction may be most conveniently conducted over a range of temperatures from $-100°$ C. to $+300°$ C., preferably in the range of from $0°$ C. to $200°$ C., and more preferably in the range of from $50°$ C. to $150°$ C.

The oligomerisation reaction may be conveniently carried out at a pressure of 0.01 to 15 MPa (0.1 to 150 bar(a)), more preferably 1 to 10 MPa (10 to 100 bar(a)), and most preferably 1.5 to 5 MPa (15 to 50 bar(a)).

The optimum conditions of temperature and pressure used for a particular catalyst system to maximise the yield of oligomer, and to minimise the competing reactions such as dimerisation and polymerisation can be readily established by one skilled in the art.

The conditions of temperature and pressure are preferably selected to yield a product slate with a K-factor within the range of from 0.50 to 0.90, most preferably in the range of from 0.60 to 0.80. In the present invention, polymerisation is deemed to have occurred when a product slate has a K-factor greater than 0.9.

The oligomerisation reaction can be carried out in the gas phase or liquid phase, or mixed gas-liquid phase, depending upon the volatility of the feed and product olefins.

The oligomerisation reaction is carried out in the presence of an inert solvent which may also be the carrier for the catalyst and/or feed olefin. Suitable solvents include alkanes, alkenes, cycloalkanes, and aromatic hydrocarbons. For example, solvents that may be suitably used according to the present invention include hexane, isooctane, benzene, toluene, and xylene.

Reaction times of from 0.1 to 10 hours have been found to be suitable, dependent on the activity of the catalyst. The reaction is preferably carried out in the absence of air or moisture.

The oligomerisation reaction may be carried out in a conventional fashion. It may be carried out in a stirred tank reactor, wherein olefin and catalyst or catalyst precursors are added continuously to a stirred tank and reactant, product, catalyst, and unused reactant are removed from the stirred tank with the product separated and the catalyst and unused reactant recycled back to the stirred tank.

Alternatively, the reaction may be carried out in a batch reactor, wherein the catalyst precursors, and reactant olefin are charged to an autoclave, and after being reacted for an appropriate time, product is separated from the reaction mixture by conventional means, such as distillation.

After a suitable reaction time, the oligomerisation reaction can be terminated by rapid venting of the ethylene in order to deactivate the catalyst system.

The resulting alpha olefins have a chain length of from 4 to 100 carbon atoms, preferably 4 to 30 carbon atoms, and most preferably from 4 to 20 carbon atoms.

Product olefins can be recovered suitably by distillation and further separated as desired by distillation techniques dependent on the intended end use of the olefins.

The present invention will now be illustrated by the following Examples, which should not be regarded as limiting the scope of the present invention in any way, by reference to the accompanying drawings, in which:—

Figure 2:
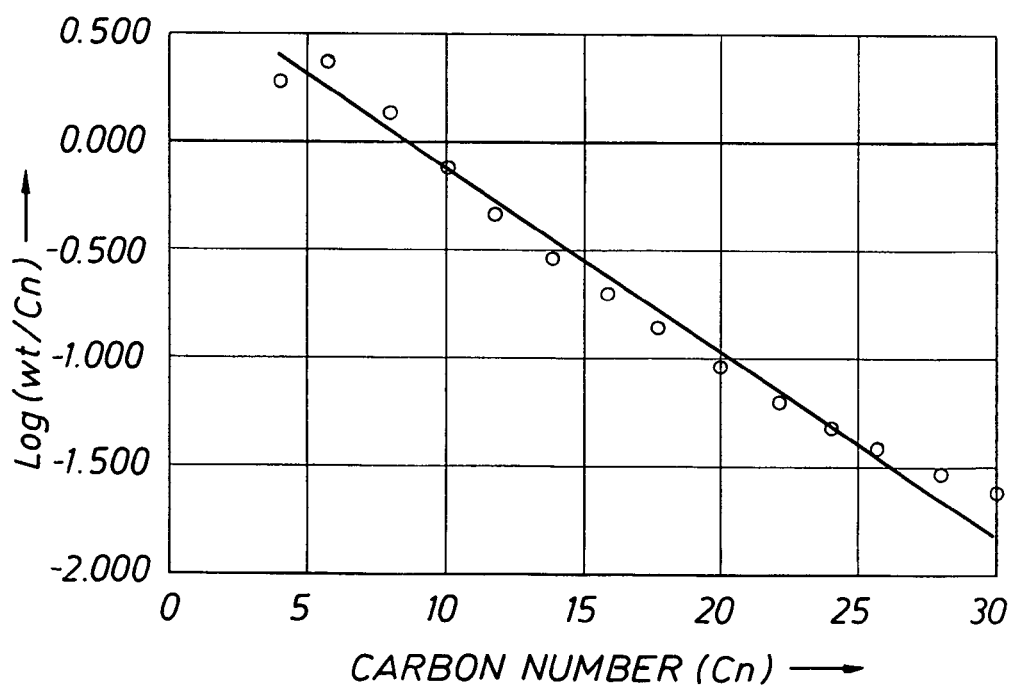
FIG. 2 is a regression analysis of Example 5.
Figure 3:
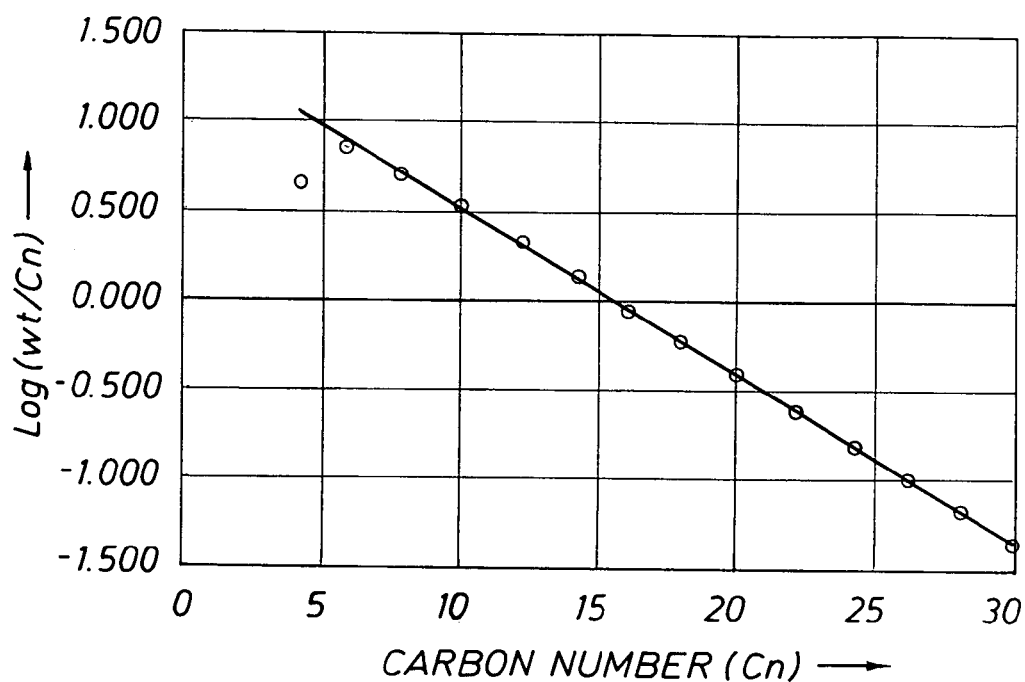
FIG. 3 is a regression analysis of Example 8.

FIG. 1 is a regression analysis of Example 2;

FIG. 2 is a regression analysis of Example 5;

FIG. 3 is a regression analysis of Example 8; and

Figure 4:
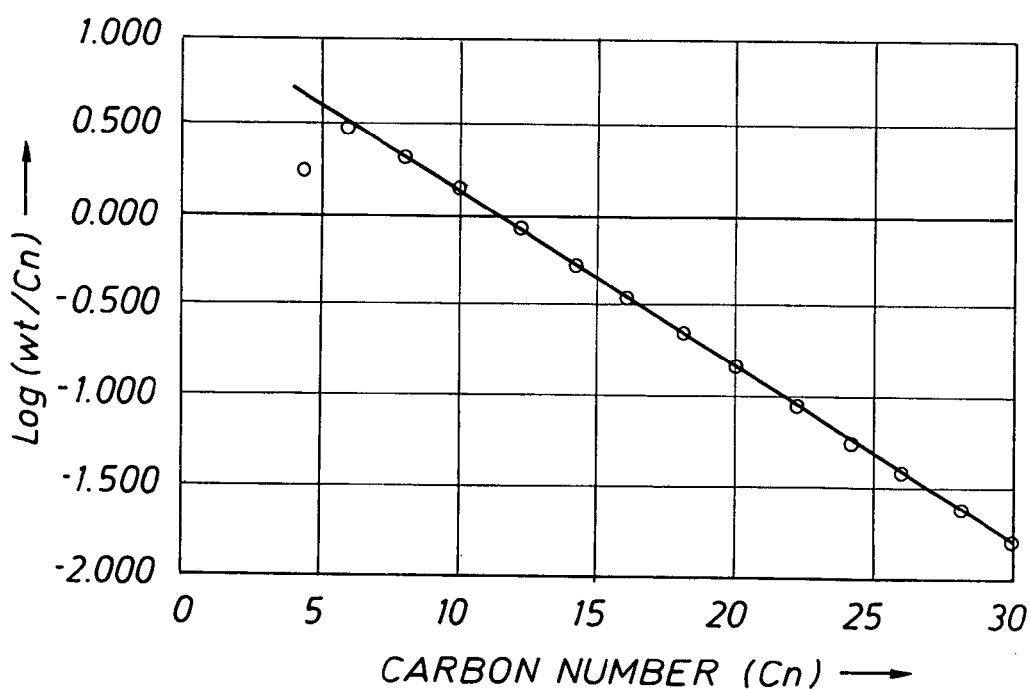
FIG. 4 is a regression analysis of Example 10.

FIG. 4 is a regression analysis of Example 10.

EXPERIMENTS

General Procedures and Characterisation

All the operations with the catalyst systems were carried out under nitrogen atmosphere.

Anhydrous toluene (99.8% purity) (ex. Aldrich) was dried over 4 Å molecular sieves (final water content of about 3 ppm).

Ethylene (99.5% purity) was purified over a column containing 4 Å molecular sieves and BTS catalyst (ex. BASF) in order to reduce water and oxygen content to <1 ppm.

2,6-Diacetylpyridine, 2,4,6-trimethylaniline, 4-tert-butylaniline, 2,6-diethylaniline and anhydrous iron (II) chloride are available ex. Aldrich. 1-Aminopyrrole was purchased from TCI, Japan.

Ferrocenylamine was prepared according to the method outlined in the literature (D. van Leusen and B. Hessen, Organometallics, 2001, 20, 224-226).

The oligomers obtained were characterised by Gas Chromatography (GC), in order to evaluate oligomer distribution using a HP 5890 series II apparatus and the following chromatographic conditions:

Column: HP-1 (cross-linked methyl siloxane), film thickness=0.25 μm, internal diameter=0.25 mm, length 60 m (by Hewlett Packard); injection temperature: 325° C.; detection temperature: 325° C.; initial temperature: 40° C. for 10 minutes; temperature programme rate: 10.0° C./minute; final temperature: 325° C. for 41.5 minutes; internal standard: n-hexylbenzene. Response factors for the even linear α-olefins, for the internal hexenes: cis- and trans-2-hexene, and cis- and trans-3-hexene, and for the branched hexenes: 3-methyl-1-pentene and 2-ethyl-1-butene, relative to n-hexylbenzene (internal standard) were determined using a standard calibration mixture. The response factors of the branched and internal dodecenes were assumed to be equal to the corresponding linear α-olefins.

The yields of the $C_4$-$C_{30}$ olefins were obtained from the GC analysis, from which the K-factor and the theoretical yield of $C_4$-$C_{100}$ olefins, i.e. total oligomerisation product (Total Product), were determined by regression analysis, using the $C_6$-$C_{28}$ data.

The relative amounts of the linear 1-hexene amongst all hexene isomers and the relative amount of 1-dodecene amongst all dodecene isomers found from the GC analysis is used as a measure of the selectivity of the catalyst towards linear alpha-olefin formation.

The NMR data were obtained at room temperature with a Varian 300 MHz or 400 MHz apparatus.

Catalyst Components

1. Preparation of 2-[1-(2,4,6-trimethylphenylimino)ethyl]-6-acetylpyridine (1)

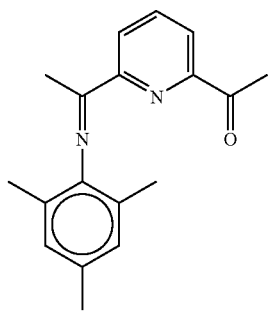

(1)

2,6-Diacetylpyridine (7.3 g, 44.8 mmol) and 2,4,6-trimethylaniline (5.74 g, 42.55 mmol) were dissolved in 450 ml of toluene. To this solution, 4 Å molecular sieves and a small amount of p-toluenesulphonic acid (0.22 mmol) were added. The mixture was refluxed for 16 h. After filtration the solvent was removed in vacuo. Several crystallisations from ethanol yielded 3.42 g (28.7%) of monoimine (1). $^1$H-NMR (CDCl$_3$) δ 8.55 (d, 1H, Py-H$_m$), 8.11(d, 1H, Py-H$_m$), 7.92 (t, 1H, Py-H$_p$), 6.89 (s, 2H, ArH), 2.77 (s, 3H, Me), 2.27 (s, 3H, Me), 2.22 (s, 3H, Me), 1.99 (s, 6H, Me).

2. Preparation of 2-[1-(2,4,6-trimethylphenylimino)ethyl]-6-[1-(4-tert-butylphenylimino)ethyl]pyridine (2)

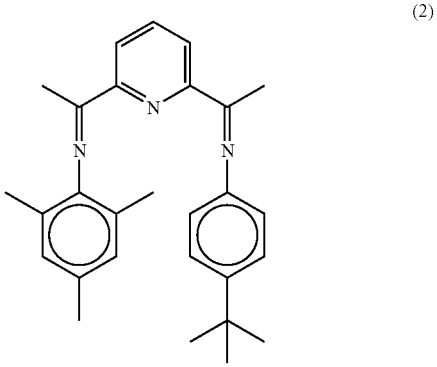

(2)

Monoimine (1, 2.8 g, 10 mmol) and 4-tert-butylaniline (1.49 g, 10 mmol) were dissolved in 100 ml of toluene. To this solution, 4 Å molecular sieves and a small amount of p-toluenesulphonic acid (0.1 mmol) were added. After standing for 5 days with addition of more 4 Å molecular sieves, the mixture was refluxed for 2 hours. After filtration the solvent was removed in vacuo. The residue was washed with methanol and recrystallised from ethanol. Yield 2.4 g (58%) of mixed diimine (2). $^1$H-NMR (CDCl$_3$) δ 8.42 (d, 1H, Py-H$_m$), 8.34 (d, 1H, Py-H$_m$), 7.86 (t, 1H, Py-H$_p$), 7.38 (d, 2H, ArH), 6.89 (s, 2H, ArH), 6.78 (d, 2H, ArH), 2.42 (s, 3H, Me), 2.29 (s,3H, Me), 2.22 (s, 3H, Me), 2.00 (s, 6H, Me), 1.34 (s, 9H, Bu$^t$).

3. Preparation of 2-[1-(2,4,6-trimethylphenylimino)ethyl]-6-[1-(4-tert-butylphenylimino)ethyl]pyridine iron[II]chloride complex, (3)

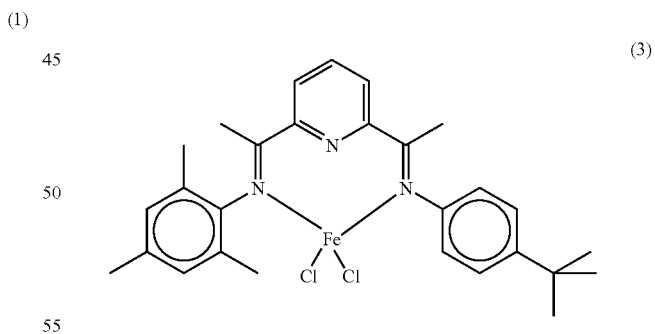

(3)

In an inert atmosphere, a solution of 1.5 g diimine (2, 3.6 mmol) in 100 ml dichloromethane was added to 420 mg FeCl$_2$ (3.3 mmol) in 150 ml dichloromethane. The mixture was stirred for one week. The developed blue precipitate was isolated by filtration and dried in vacuo. Yield 1.5 g (84%) of iron complex (3). $^1$H-NMR (Cl$_2$CDCDCl$_2$, broad signals) d 79.3 (1H, Py-H$_m$), 77.7 (1H, Py-H$_m$), 27.0 (1H, Py-H$_p$), 20.7 (3H, Me), 17.3 (6H, Me), 15.0 (2H, ArH), 14.3 (2H, ArH), 1.2 (9H, Bu$^t$), −2.6 (3H, MeC=N), −17.9 (2H, o-ArH), −32.1 (3H, MeC=N).

4. Preparation of 2,6-bis[1-(ferrocenylimino)ethyl]pyridine (4)

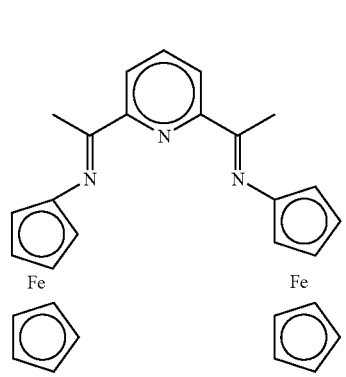
(4)

In an inert atmosphere, 2,5-diacetylpyridine (50 mg, 0.30 mmol) and ferrocenylamine (123.4 mg, 0.61 mmol) were dissolved in 50 ml of toluene. To this solution, molecular sieves (4 Å) were added. After standing for 65 hours at room temperature the mixture was filtered. The solvent was removed in vacuo. The residue was crystallised from ethanol. Yield 75 mg (46%) red crystals of diimine 4. $^1$H-NMR (CDCl$_3$) δ 8.26 (d, 2H, Py-H$_m$), 7.78 (t, 1H, Py-H$_p$), 4.43 (t, 4H, CpH), 4.22 (t, 4H, CpH), 4.21 (s, 10H, CpH), 2.54 (s, 6H, Me).

5. Preparation of 2,6-bis[1-(ferrocenylimino)ethyl]pyridine iron[II]chloride complex (5)

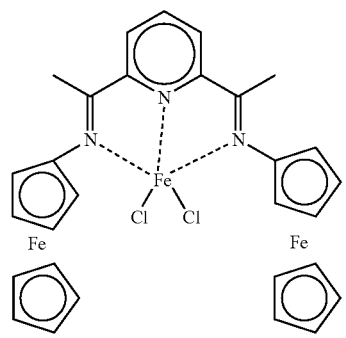
(5)

In an inert atmosphere, a red solution of 390 mg diimine (4, 0.737 mmol) in 10 ml dichloromethane was added to 89 mg FeCl$_2$ (0.702 mmol) in 10 ml dichloromethane. The mixture was stirred for 16 hours. After addition of 6 ml hexane the blue precipitate was isolated by centrifugation, washed with hexane and dried in vacuo. Yield 200 mg (44%) of iron complex 5. $^1$H-NMR (CD$_2$Cl$_2$, broad signals) δ 83.0 (2H, Py-H$_m$), 9.3 (4H, CpH), 3.3 (10H, CpH), 2.7 (6H, MeC=N), −1.5 (4H, CpH), −5.2 (1H, Py-H$_p$).

6. Preparation of 2-[1-(2,4,6-trimethylphenylimino)ethyl]-6-[1-(ferrocenylimino)ethyl]pyridine (6)

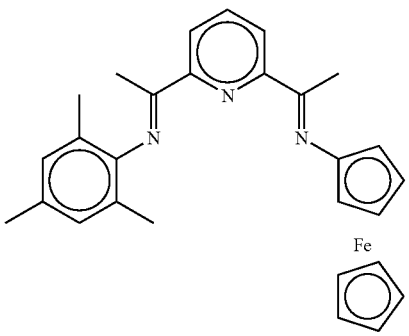
(6)

Monoimine 2-[1-(2,4,6-trimethylphenylimino)ethyl]-6-acetylpyridine (1, 263 mg, 0.94 mmol) and ferrocenylamine (280 mg, 1.03 mmol) were dissolved in 40 ml of toluene. To this solution, molecular sieves (4 Å) were added. After standing for 16 hours the mixture was filtered. The solvent was removed in vacuo. The residue was recrystallised from ethanol. Yield 180 mg (41%) of mixed diimine 6.
$^1$H-NMR (CD$_2$Cl$_2$) δ 8.36 (dd, 2H, Py-H$_m$), 7.85 (t, 1H, Py-H$_p$), 6.88 (s, 2H, ArH), 4.46 (t, 2H, CpH), 4.25 (t, 2H, CpH), 4.20 (s, 5H, CpH), 2.55 (s, 3H, Me), 2.27 (s, 3H, Me), 2.20 (s, 3H, Me), 1.98 (s, 6H, Me).

7. Preparation of 2-[1-(2,4,6-trimethylphenylimino)ethyl]-6-[1-(ferrocenylimino)ethyl]pyridine iron[II] chloride complex (7)

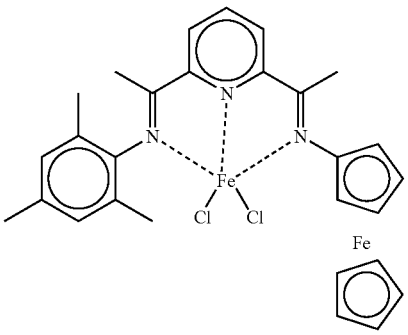
(7)

In an inert atmosphere, a solution of 153 mg diimine (6, 0.33 mmol) in 5 ml dichloromethane was added to 41 mg FeCl$_2$ (0.32 mmol) in 5 ml dichloromethane. The mixture was stirred for 16 hours. The blue-gray precipitate was isolated by centrifugation, washed with hexane and dried in vacuo. Yield 170 mg (89%) of iron complex 7.
$^1$H-NMR (CD$_2$Cl$_2$, broad signals, selected data) δ 88.6 (1H, Py-H$_m$), 76.7 (1H, Py-H$_m$), 21.3 (3H, Me), 16.3 (6H, Me), 2.8 (5H, CpH), −11.5 (3H, MeC=N).

8. Preparation of 2-[1-(2,6-diethylphenylimino) ethyl]-6-acetylpyridine (8)

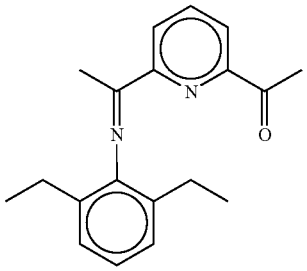

(8)

2,6-Diacetylpyridine (8.15 g, 50 mmol) and 2,6-diethylaniline (7.46 g, 50 mmol) were dissolved in toluene (150 ml). To this solution, molecular sieves (4 Å) were added. Two drops of concentrated sulphuric acid were added and subsequently the mixture was refluxed for 16 hours, which resulted in a 73% conversion. The solvent was removed in vacuo.

The resulting mixture of 2,6-diacetylpyridine, 2,6-bis-[1-(2,6-diethylphenylimino)ethyl]pyridine and 2-[1-(2,6-diethylphenylimino)ethyl]-6-acetylpyridine was crystallised from ethanol and yielded a 3:1 mixture of 2-[1-(2,6-diethylphenylimino)ethyl]-6-acetylpyridine and 2,6-bis-[1-(2,6-diethylphenylimino)ethyl]pyridine.

This mixture was dissolved in THF (75 ml), the diimine by-product was removed by selective complexation with a metal halide. To that end an equimolar amount of FeCl$_2$ (0.75 g, 5.93 mmol) was added in an inert atmosphere. After stirring for 16 hours at room temperature, the solvent was removed in vacuo.

Toluene (75 ml) was added to the resulting mixture. The precipitated complex was filtered off over a thin layer of silica, yielding a yellow solution. The solvent was removed in vacuo.

Crystallisation from ethanol yielded 3.05 g of 2-[1-(2,6-diethylphenylimino)ethyl]-6-acetylpyridine (21%).

$^1$H-NMR (CDCl$_3$) δ 8.55 (dd, 1H, Py-H$_m$), 8.12 (dd, 1H, Py$_m$), 7.93 (t, 1H, Py$_p$), 7.11 (d, 2H, ArH$_m$), 7.03 (dd, 1H, ArH$_p$), 2.78 (s, 3H, Me), 2.36 (m, 4H, CH$_2$), 2.24 (s, 3H, Me), 1.13 (t, 6H, Me).

9. Preparation of 2-[1-(2,6-diethylphenylimino) ethyl]-6-[1-(ferrocenylimino)ethyl]pyridine (9)

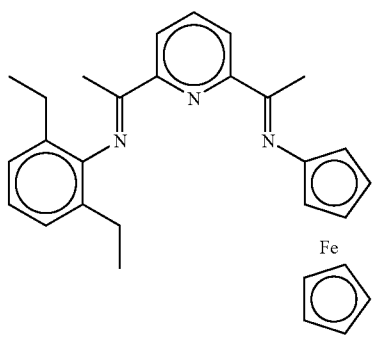

(9)

In an inert atmosphere, monoimine 2-[1-(2,6-diethylphenylimino)ethyl]-6-acetylpyridine (8, 368 mg, 1.25 mmol) and ferrocenylamine (268 mg, 1.33 mmol) were dissolved in 50 ml of toluene. To this solution, molecular sieves (4 Å) were added. After standing for 40 hours the mixture was filtered. The solvent was removed in vacuo. The residue was recrystallised from ethanol. Yield 160 mg (27%) red crystals of mixed diimine 9.

$^1$H-NMR (CD$_2$Cl$_2$) δ 8.38 (d, 1H, Py-H$_m$), 8.35 (d, 1H, Py-H$_m$), 7.87 (t, 1H, Py-H$_p$), 7.10 (d, 2H, ArH), 7.01 (t, 1H, ArH), 4.46 (t, 2H, CpH), 4.26 (t, 2H, CpH), 4.21 (s, 5H, CpH), 2.56 (s, 3H, Me), 2.36 (m, 4H, CH$_2$), 2.22 (s, 3H, Me), 1.11 (t, 6H, Me).

10. Preparation of 2-[1-(2,6-diethylphenylimino) ethyl]-6-[1-(ferrocenylimino)ethyl]pyridine iron[II] chloride complex (10)

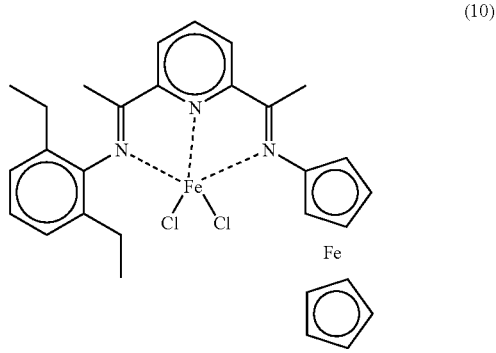

(10)

In an inert atmosphere, a red solution of 100 mg diimine (9, 0.21 mmol) in 5 ml dichloromethane was added to 25.7 mg FeCl$_2$ (0.20 mmol) in 5 ml dichloromethane. The mixture was stirred for 65 hours. After addition of 5 ml hexane, the blue-gray precipitate was isolated by centrifugation, washed with hexane and dried in vacuo. Yield 100 mg (82%) of iron complex 10.

$^1$H-NMR (CD$_2$Cl$_2$, broad signals, selected data) δ 88.5 (1H, Py-H$_m$), 75.3 (1H, Py-H$_m$), 16.3 (2H, CH$_a$H$_b$), 13.2 (2H, CH$_a$H$_b$), 2.5 (5H, CpH), 0.8 (6H, Me), −4.6 (1H, ArH), −12.5 (3H, MeC=N), −14.5 (2H, CpH).

11. Preparation of 2,6-bis[1-(1-pyrrolylimino)ethyl]pyridine (11)

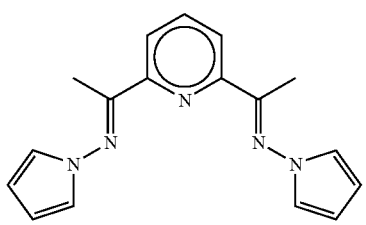

(11)

2,6-Diacetylpyridine (345 mg, 2.11 mmol) and 1-aminopyrrole (400 mg, 4.87 mmol) were dissolved in 50 ml of toluene. To this solution, molecular sieves (4 Å) were added. After standing for 2 days at room temperature, the mixture was filtered. The solvent was removed in vacuo. The residue was crystallised from ethanol. Yield 350 mg (57%) of diimine 11.

$^1$H-NMR (CDCl$_3$) δ 8.26 (d, 2H, Py-H$_m$), 7.82 (t, 1H, Py-H$_p$), 6.93 (m, 2H, PyrH), 6.25 (m, 2H, PyrH), 2.66 (s, 6H, Me).

12. Preparation of 2,6-bis[1-(1-pyrrolylimino)ethyl]pyridine iron[II]chloride complex (12)

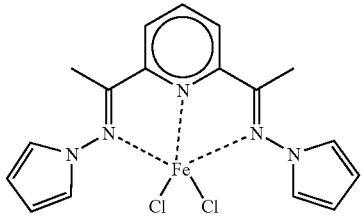

(12)

In an inert atmosphere, a solution of 26 mg FeCl$_2$ (0.27 mmol) in 0.4 ml ethanol was slowly added to a solution of 80 mg diimine (11, 0.27 mmol) in 3 ml toluene. The developed blue precipitate was isolated by centrifugation, washed three times with toluene and dried in vacuo. Yield 75 mg of iron complex 12.

NMR did not reveal any signals for this complex.

13. Preparation of 2-[1-(2,6-diethylphenylimino)ethyl]-6-[1-(1-pyrrolylimino)ethyl]pyridine (13)

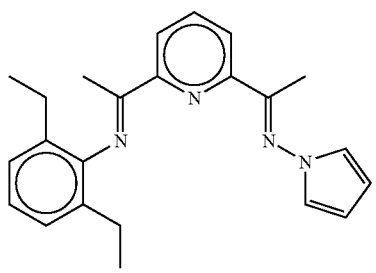

(13)

Monoimine 2-[1-(2,6-diethylphenylimino)ethyl]-6-acetylpyridine (8, 1.5 g, 5.1 mmol) and 1-aminopyrrole (460 mg, 5.6 mmol) were dissolved in 25 ml of toluene. To this solution, molecular sieves (4 Å) were added. After standing for 16 hours the mixture was filtered. The solvent was removed in vacuo. The residue was crystallised from ethanol. Yield 845 mg (46%) of mixed diimine 13.

$^1$H-NMR (CDCl$_3$) δ 8.41 (d, 1H, Py-H$_m$), 8.29 (d, 1H, Py-H$_m$), 7.86 (t, 1H, Py-H$_p$), 6.98-7.14 (m, 3H, ArH), 6.93(m, 2H, PyrH), 6.25 (m, 2H, PyrH), 2.67 (s, 3H, Me), 2.36 (m, 4H, CH$_2$), 2.21 (s, 3H, Me), 1.12 (t, 6H, Me).

14. Preparation of 2-[1-(2,6-diethylphenylimino)ethyl]-6-[1-(1-pyrrolylimino)ethyl]pyridine iron[II] chloride complex (14)

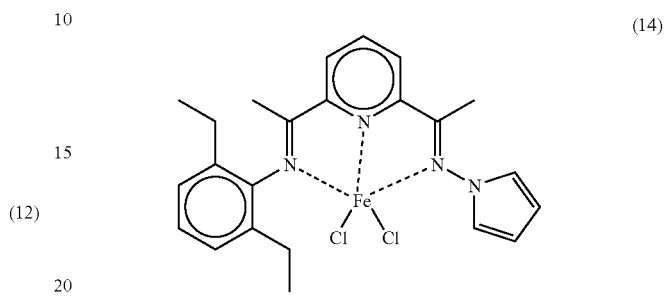

(14)

In an inert atmosphere, a solution of 211 mg diimine (13, 0.59 mmol) in 5 ml dichloromethane was added to 70 mg FeCl$_2$ (0.55 mmol) in 10 ml dichloromethane. The mixture was stirred for 60 hours. After addition of 15 ml of hexane the blue precipitate was isolated by centrifugation, washed with hexane and dried in vacuo. Yield 250 mg (93%) of iron complex 14.

$^1$H-NMR (CD$_2$Cl$_2$, broad signals) δ 87.3 (1H, Py-H$_m$), 72.2 (1H, Py-H$_m$), 27.9 (3H, Me), 18.3 (2H, CH$_a$H$_b$), 14.8 (2H, CH$_a$H$_b$), 14.4 (2H, ArH), 8.5 (2H, PyrH), 4.6 (2H, PyrH), 1.2 (1H, Py-H$_p$), 0.2 (6H, Me), −10.8 (1H, ArH), −43.4 (1H, MeC=N),

15. Preparation of 2-[1-(2,4,6-trimethylphenylimino)ethyl]-6-[1-(1-pyrrolylimino)ethyl]pyridine (15)

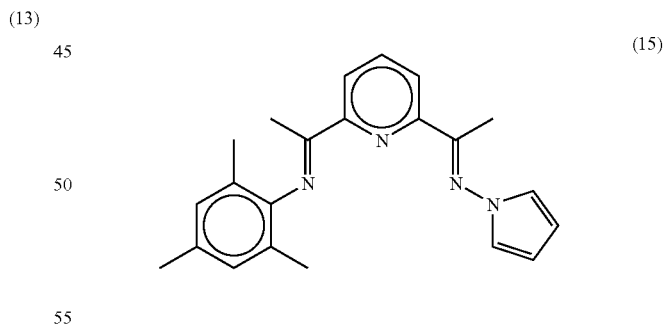

(15)

Monoimine (1, 3.0 g, 10.7 mmol) and 1-aminopyrrole (1.0 g, 12.18 mmol) were dissolved in 50 ml of toluene. To this solution, molecular sieves (4 Å) were added. After standing for 40 hours the mixture was filtered. The solvent was removed in vacuo. The residue was crystallised from ethanol. Yield 1.85 g (50%) of mixed diimine 15.

$^1$H-NMR (CDCl$_3$) δ 8.42 (d, 1H, Py-H$_m$), 8.29 (d, 1H, Py-H$_m$), 7.86 (t, 1H, Py-H$_p$), 6.93 (m, 2H, Pyrrole-H), 6.88 s, 2H, ArH), 6.26 (m, 2H, Pyrrole-H), 2.67 (s, 3H, Me), 2.28 (s, 3H, Me), 2.20 (s, 3H, Me), 2.00 (s, 6H, Me).

16. Preparation of 2-[1-(2,4,6-trimethylphenylimino)ethyl]-6-[1-(1-pyrrolylimino)ethyl]pyridine iron[II]chloride complex (16)

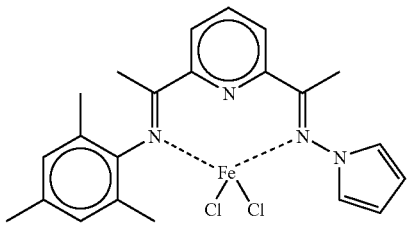

(16)

In an inert atmosphere, a solution of 103 mg $FeCl_2$ (0.81 mmol) in 0.7 ml ethanol was slowly added to a solution of 400 mg diimine (15, 1.16 mmol) in a solvent mixture of 10 ml toluene and 6 ml pentane. The green-brown precipitate was isolated by centrifugation, washed three times with toluene and dried in vacuo. Yield 375 mg (98%) of iron complex 16.

$^1$H-NMR ($CD_2Cl_2$, broad signals, not assigned) δ 88.1 (1H), 72.4 (1H), 29.9 (3H), 19.5 (3H), 16.9 (6H), 13.5 (2H), 8.8 (2H), 5.8 (2H), 2.9 (1H), −45.1 (3H).

17. Alternate preparation of 2-[1-(2,4,6-trimethylphenylimino)ethyl]-6-[1-(1-pyrrolylimino) ethyl] pyridine iron[II]chloride complex (16')

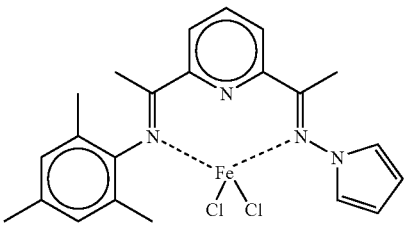

(16')

In an inert atmosphere, a solution of 204 mg mixed diimine (15, 0.59 mmol) in 5 ml dichloromethane was added to 70 mg $FeCl_2$ (0.55 mmol) in 10 ml dichloromethane. The mixture was stirred for 65 hours. The resulting green-brown precipitate was isolated by centrifugation, washed with pentane and dried in vacuo. Yield 200 mg (77%) of iron complex 16'.

$^1$H-NMR ($CD_2Cl_2$, broad signals, not assigned) δ 88.1 (1H), 72.5 (1H), 29.8 (3H), 19.6 (3H), 16.9 (6H), 13.6 (2H), 8.8 (2H), 5.7 (2H), 3.6 (1H), −45.2 (3H).

18. Preparation of 2,6-[1-(2-methylphenylimino)ethyl]pyridine iron[II]chloride complex (X)

Complex X was prepared according to the method disclosed in WO-A-99/02472.

19. Methylaluminoxane (MAO)

The MAO-solutions in toluene (Eurecen AL 5100/10T, batch: B7683; [Al]=4.88% wt, TMA=35.7 wt %(calculated), Molecular mass=900 g/mol and [Al]=4.97% wt) used in the experiments were ex. Witco GmbH, Bergkamen, Germany.

20. Solutions in Toluene of Triethylaluminium (25% wt TEA) and of Tri-isobutylaluminium (25% wt TIBA) are available from Aldrich Catalyst System Preparation Catalyst preparation was carried out under nitrogen in a Braun MB 200-G dry box.

The iron complex (typically about 10 mg) was placed in a glass bottle sealed by a septum; the MAO-solution (4.0 g), of the above mentioned grade, or the alternate co-catalyst in the amounts indicated in Tables 1 and 2 (see "Premix co-catalyst/Molar ratio Al:Fe" in Table 2), was added and stirred for 2 minutes. This yielded generally a dark-coloured solution, which sometimes contained some precipitate. Thereafter toluene (9.0 g) was added and the solution was stirred for another 10 min. Immediately hereafter, part of this mixture, i.e. the catalyst premix, was added to a 1-liter or 0.5-liter steel autoclave via its injection system and used in the oligomerisation reaction (see Tables 1 and 2 for the amounts used).

Oligomerisation Experiments

Oligomerisation experiments were carried out in a 1-liter or a 0.5-liter steel autoclave equipped with jacket cooling with a heating/cooling bath (ex. Julabo, model no. ATS-2) and a turbine/gas stirrer and baffles.

In order to remove traces of water from the reactor, it was evacuated overnight at <10 Pa, at 70° C. The reactor was scavenged by introducing 250 ml toluene and MAO (0.3-1.2 g solution) and subsequent stirring at 70° C. under nitrogen pressure of 0.4-0.5 MPa for 30 min. The reactor contents were discharged via a tap in the base of the autoclave. The reactor was evacuated to 0.4 kPa and loaded with 250 ml toluene and heated to 40° C. and pressurised with ethylene to the pressure indicated in Tables 1 and 2 or in the description of the experiment.

The MAO-solution (typically 0.5 g for a 1-liter autoclave and typically 0.25 g for a 0.5-liter autoclave) was then added to the reactor with the aid of toluene (the total volume injected was 30 ml, using a procedure similar to the injection of the catalyst premix; see below) and the stirring at 800 rpm was continued for 30 minutes.

The catalyst system prepared as described above and in an amount as described in Tables 1 and 2, was introduced into the stirred reactor using an injection system with the aid of toluene (the total volume injected was 30 ml: the catalyst pre-mix diluted with toluene to 10 ml was injected and the injector system was rinsed twice with 10 ml toluene).

In the case of an active catalyst system, the addition of the catalyst pre-mix resulted in an exotherm (generally 5-20° C.), which generally reached a maximum within 1 minute and was followed by rapid establishment of the temperature and pressure indicated in Tables 1 and 2.

Temperature and pressure were monitored throughout the reaction, as well as ethylene consumption, whilst maintaining a constant ethylene pressure.

After consuming a certain volume ethylene, the oligomerisation was stopped by rapid venting of the ethylene, decanting the product mixture into a collection bottle using a tap in the base of the autoclave. Exposure of the mixture to air resulted in rapid deactivation of the catalyst.

After addition of n-hexylbenzene (0.5-3.5 g) as internal standard to the crude product, the amount of $C_4$-$C_{30}$ olefins was determined by gas chromatography, from which the (apparent) Schulz-Flory K-factor was determined by regression analysis, generally using the $C_6$-$C_{28}$ data of the linear alpha olefins.

By "apparent K-factor" is meant the K-factor in the case that there is a small deviation from a Schulz-Flory distribution. From this regression analysis, the theoretical contents of $C_{30}$-$C_{100}$ components, i.e. waxy solids, was calculated. The data are reported in Table 1.

The amount of solids in the product was determined as follows. The crude reaction product was centrifuged at 4000 rpm for 30 min after which the clear upper layer was decanted. The lower layer consisting of solid olefins, toluene and a minor amount of liquid olefins was mixed with 500 ml acetone using a high-shear mixer (Ultra-Turrax, type TP 18-10). The mixture was centrifuged under the above-mentioned conditions. The lower layer was mixed with 200 ml acetone and filtered off over a glass filter (porosity P3). The solid product was dried for 24 hours at 70° C. at <1 kPa, weighed and its $<C_{30}$ contents determined by gas chromatography of a 1,2-dichlorobenzene or a 1,2,4-trichlorobenzene solution of the solids. The amounts of solids reported in Table 1 are the isolated solids having a carbon number $>C_{28}$.

The relative amounts of the linear 1-hexene amongst all hexene isomers and the relative amount of the linear 1-dodecene amongst all dodecene isomers were evaluated by GC analysis and are reported in Tables 1 and 2.

EXAMPLE 1

Comparative

Example 1a was carried out at an average ethylene pressure of 1.7 MPa, i.e. 1.6 MPa (gauge), using the iron complex 5 which is not in accordance with the present invention. Experimental details are given in Table 1. The activated iron complex was added in 5 portions (270, 550, 1510, 4570 and 9100 nmol at time=0, 3, 11, 13, 23 min) and an additional portion of MAO-solution was added (1.0 g MAO-solution at time=25 min). After 14 min the temperature was raised from 50 to 70° C. and kept at that temperature for the remainder of the experiment. Very little, if any, ethylene conversion took place, even after having added the relatively large total amount of this symmetrical iron bis-imine pyridine catalyst and MAO and after increase of the temperature.

To check that the autoclave system was not compromised by ingress of air or moisture Example 1a was extended by addition of the activated non-symmetrical iron catalyst 3 (see Example 1b in Table 1) of co-pending patent application PCT/EP01/01506 at 1.5 MPa ethylene pressure at 40° C., followed by rapid increase of the temperature to 70° C. The activity of catalyst 3, the product distribution and the product purity are in line with those observed for 3 in the above-mentioned co-pending patent application, despite the presence of relatively large amounts of catalyst 5 and MAO.

EXAMPLE 2

Example 2 was carried out at an average ethylene pressure of 1.7 MPa, using the mixed aryl-, ferrocenylimine iron complex 7 which is in accordance with the present invention. Experimental details are given in Table 1. The catalyst gave a Turn Over Frequency (TOF) of 2.45E+06 mol ethylene/mol Fe*h and afforded a product of high 1-hexene and 1-dodecene purity. It is noted that the product distribution showed a clear deviation from a Schulz-Flory distribution, particularly at low carbon numbers, as shown in FIG. 1 (regression statistics: $R^2$=0.98; standard error=0.08 for 12 data points).

EXAMPLE 3

Example 3 was carried out at an average ethylene pressure of 1.6 MPa, using the mixed aryl-, ferrocenylimine iron complex 10 which is in accordance with the present invention. Experimental details are given in Table 1. The catalyst gave a TOF of 1.97E+06 mol ethylene/mol Fe*h and afforded a product of lower 1-hexene and 1-dodecene purity than that Example 2. It is noted that the product distribution showed an even clearer deviation from a Schulz-Flory distribution than that of Example 2 (regression statistics: $R^2$=0.81; standard error=0.25 for 12 data points). This is confirmed by the amounts of waxy solids $>C_{28}$ isolated on total product of 8.4% wt for Example 3, whereas the K-factor gives rise to a $C_{30}$-$C_{100}$ fraction on total oligomerisation product of 6.5% wt.

EXAMPLE 4

Comparative

Example 4a was carried out at an average ethylene pressure of 1.7 MPa, using the bis-[1-pyrrolylimine]iron complex 12 which is not in accordance with the present invention. Experimental details are given in Table 1. The activated iron complex was added in 4 portions (3100, 3100, 6200 and 13600 nmol at time=0, 3, 4, 11 min). At time=10 min the temperature was raised from 50 to 70° C. and kept at that temperature for 10 min. At time=20 min the temperature was decreased to 40° C. and kept at that temperature for the remainder of the experiment. Very little, if any, ethylene conversion took place, even after having added the relatively large total amount of this iron bis-imine pyridine catalyst and after increase of the temperature to 70° C.

To check that the autoclave system was not compromised by ingress of air or moisture Example 4a was extended by addition of the activated non-symmetrical iron catalyst 3 (see Example 4b in Table 1) of co-pending patent application PCT/EP01/01506 at 1.5 MPa ethylene pressure and at 40° C., followed by increase of the temperature to 70° C. The activity of catalyst 3, the product distribution and the product purity are in line with those observed for 3 in the above-mentioned co-pending patent application, despite the presence of relatively large amounts of catalyst 12 and MAO.

It is noted that the iron bis-imine pyridine catalyst derived from 2,5-dimethylaminopyrrole, also not according to this invention, as described in patent application WO 00/50470 to Eastman Chemical Company, Example 58, which is to be considered to be a higher homologue of catalyst 12, has a high ethylene conversion activity, T.O.F=4.14E+06 mol/mol*h, but gives rise to the formation of polyethylene, $M_n$(NMR)=1154 (Examples 60 and 59 of WO 00/50470, respectively), instead of alpha olefins in the $C_4$-$C_{30}$ range.

EXAMPLE 5

Example 5 was carried out at an average ethylene pressure of 1.6 MPa, i.e. 1.5 MPa (gauge), using the non-symmetrical iron complex 14 which is in accordance with the present invention. Experimental details are given in Table 1. The regression analysis using the $C_6$-$C_{28}$ contents, as shown in FIG. 2, gives a clear deviation from a Schulz-Flory distribution. The K-factor is 0.678 (regression statistics for 12 observations: $R^2$=0.98 and standard error=0.08). This is confirmed by the amounts of waxy solids $>C_{28}$ isolated on total product of 13.8% wt for Example 5, whereas the K-factor gives rise to a $C_{30}$-$C_{100}$ fraction on total oligomerisation product of 2.6% wt. The T.O.F. of the catalyst is 1.45E+07 mol ethylene/mol Fe*h and the 1-hexene and 1-dodecene purity is 99.5% and 98.4%, respectively.

EXAMPLE 6

Example 6 is a repeat of Example 5 at a higher [Al]/[Fe] ratio. The results, given in Table 1, are similar to those of Example 5. Again a clear deviation from a S—F distribution is observed ($R^2$=0.98; standard error=0.09 for 12 data points). This is confirmed by the amounts of waxy solids >$C_{28}$ isolated on total product of 12.2% wt, whereas the K-factor gives rise to a $C_{30}$-$C_{100}$ fraction on total oligomerisation product of 1.9% wt.

EXAMPLE 7

Example 7 is a repeat of Example 6 at a lower ethylene intake. The results, given in Table 1, indicate the tendency for a lower apparent K-factor under these conditions. Yet again a clear deviation from a S—F distribution is observed ($R^2$=0.99; standard error=0.09 for 12 data points). This is confirmed by the amounts of waxy solids >$C_{28}$ isolated on total product of 5.1% wt for Example 7, whereas the K-factor gives rise to a $C_{30}$-$C_{100}$ fraction on total oligomerisation product of 1.0% wt.

EXAMPLE 8

Example 8 was carried out at an average ethylene pressure of 1.5 MPa, i.e. 1.4 MPa (gauge), using the mixed aryl-, 1-pyrrolylimine iron complex 16 which is in accordance with the present invention. Experimental details are given in Table 1. The regression analysis using the $C_6$-$C_{28}$ contents, as shown in FIG. 3, gives surprisingly a nearly perfect Schulz-Flory distribution over the whole range of oligomers. The K-factors is 0.649 (regression statistics for 12 observations: $R^2$=1.00 and standard error=0.01). This is confirmed by the amounts of waxy solids >$C_{28}$ isolated on total product of 1.0% wt for Example 8, whereas the K-factor gives rise to a $C_{30}$-$C_{100}$ fraction on total oligomerisation product of 1.6% wt (the fact that less solids >$C_{28}$ are isolated than theoretically expected, is due to their solubility in the toluene-solution of the <$C_{28}$ oligomers). The T.O.F. the catalyst system is 2.95E+07 mol ethylene/mol Fe*h. The hexene fraction has the following composition: 1-hexene=99.0% wt, cis-2-hexene=0.0% wt, trans-2-hexene=0.2% wt, 3-hexenes=0.2% wt, branched hexenes=0.5% wt.

In conclusion it may be stated that with this mixed bis-imine iron catalyst system surprisingly no deviation from Schulz-Flory distribution is observed, which translates to the formation of less high molecular weight products in comparison with Examples 3, 5, 6 and 7. This has the advantage of more straightforward processing (less clogging by solids in the plants and its work-up train) and of less need for reprocessing of high molecular weight olefins (to render the technology economically feasible).

EXAMPLE 9

Example 9 is a repeat of Example 8, but at a lower average ethylene pressure and a lower ethylene intake. Experimental details are mentioned in Table 1. Once again, regression analysis using the $C_6$-$C_{28}$ contents gives a nearly perfect Schulz-Flory distribution, having K-factor of 0.671 and the following regression statistics for 12 observations: $R^2$=1.00 and standard error=0.01. The Schulz-Flory distribution is yet again confirmed by the isolated amount of waxy solids >$C_{28}$, which is lower than the amounts calculated from the K-factor.

EXAMPLE 10

Example 10 is a repeat of Example 8, but using catalyst precursor 16' instead of 16 and a lower ethylene intake, i.e. intake similar to that of Example 9. Experimental details are mentioned in Table 1. Once again, regression analysis using the $C_6$-$C_{28}$ contents gives a nearly perfect Schulz-Flory distribution, having K-factor of 0.645 and the following regression statistics for 12 observations: $R^2$=1.00 and standard error=0.02 (see FIG. 4). The Schulz-Flory distribution is yet again confirmed by the isolated amount of waxy solids >$C_{28}$, which is lower than the amounts calculated from the K-factor. The hexene fraction has the following composition: 1-hexene=99.5% wt, cis-2-hexene=0.0% wt, trans-2-hexene=0.1% wt, 3-hexenes=0.1% wt, branched hexenes=0.3% wt.

The activity of catalyst 16' in Example 10 appears to be higher than that of 16 in Example 8, whereas the K-factor remains the same within the limits of error and the 1-hexene purity and 1-dodecene purity are even higher.

In conclusion, it may be stated that surprisingly in the case of using this mixed bis-imine iron complex no deviation from Schulz-Flory distribution occurs, which is beneficial to the economics of the overall process, since in this case no additional amounts of solids, i.e. heavy wax, are being formed which need to be processed (which may in itself be cumbersome due to clogging, etc. of the plant and/or its work-up train) by isomerisation and disproportionation with e.g. 2-butene to arrive at internal olefins in the economically attractive range ($C_8$-$C_{20}$). Moreover, the catalyst activity of these new non-symmetrical catalyst systems is on a par with the catalysts of the co-pending patent application PCT/EP01/01506 and the 1-hexene and 1-dodecene purity is similar.

These examples prove the beneficial effects which can be achieved with the catalyst systems of the present invention. As explained above, these improvements are of major importance for the economic attractiveness of the process.

TABLE 1

|  | Example No. | | | | | |
| --- | --- | --- | --- | --- | --- | --- |
|  | Ex. 1a | Ex. 1b[1,3] | Ex. 2 | Ex. 3 | Ex. 4a | Ex. 4b[1,3] |
| Iron Complex/ (Intake in nmol) | 5(16000) | 5 + 3(539) | 7(1320) | 10(1860) | 12(26000) | 12 + 3(220) |

TABLE 1-continued

| | Ex. 1a | Ex. 1b[1,3] | Ex. 2 | Ex. 3 | Ex. 4a | Ex. 4b[1,3] |
|---|---|---|---|---|---|---|
| [Al]/[Fe] (mol/mol) | 700 | 22000(700)[4] | 1500 | 900 | 400 | 48000(400)[4] |
| Reaction Time (min) | 28 | 44 | 47 | 41 | 34 | 8 |
| Ethene Pressure MPa (bar(a)) | 1.7(17) | 1.5(15) | 1.7(17) | 1.6(16) | 1.7(17) | 1.5(15) |
| Ethene consumed (Total Product) (g) | <2.0 | 115.1 | 70.4 | 70.4 | <3.9 | 47.3[2] |
| Isolated Product <C30 (g) | 0.0 | 82.4 | 35.6 | 23.9 | 0.0 | 41.4 |
| Isolated Solids >C28 (g) | 0.0 | n.d. | 2.3 | 6.0 | 0.0 | 0.9 |
| Solids >C28 on Ethene (% wt) | n.d. | n.d. | 3.3 | 8.4 | n.d. | 1.8 |
| C30-100 on Total Product (calc'd) (% wt) | n.d. | 4.3 | 5.3 | 6.5 | n.d. | 3.1 |
| T.O.F (molC2=/molFe*h) | <1E+04 | 1.04E+07 | 2.45E+06 | 1.97E+06 | <1E+04 | 5.61E+07 |
| K-factor | n.d. | 0.706 | 0.720 | 0.732 | n.d. | 0.687 |
| 1-$C_6$ = purity (% wt) | n.d. | 98.5 | 96.9 | 92.1 | n.d. | 97.7 |
| 1-$C_{12}$ = purity (% wt) | n.d. | 96.8 | 97.7 | 92.7 | n.d. | 97.5 |
| Iron Complex/ (Intake in nmol) | 14(294) | 14(332) | 14(153) | 16(180) | 16(330) | 16'(111) |
| [Al]/[Fe] (mol/mol) | 4500 | 11300 | 11400 | 7000 | 4100 | 11500 |
| Reaction Time (min) | 38 | 38 | 12 | 114 | 21 | 36 |
| Ethene Pressure MPa (bar(a)) | 1.6(16) | 1.6(16) | 1.6(16) | 1.5(15) | 1.0(10) | 1.5(15) |
| Ethene consumed (Total Product) (g) | 76.3 | 69.3 | 29.4 | 281.8 | 117.5 | 117.4 |
| Isolated Product <C30 (g) | 58.2 | 47.4 | 25.8 | 222.6 | 98.8 | 88.3 |
| Isolated Solids >C28 (g) | 10.5 | 8.4 | 1.5 | 2.7 | 2.1 | 0.4 |
| Solids >C28 on Ethene (% wt) | 13.8 | 12.2 | 5.1 | 1.0 | 1.8 | 0.5 |
| C30-100 on Total Product (calc'd) (% wt) | 2.6 | 1.9 | 1.0 | 1.6 | 2.4 | 1.5 |
| T.O.F (molC2=/molFe*h) | 1.45E+07 | 1.19E+07 | 3.52E+07 | 2.95E+07 | 3.63E+07 | 6.34E+07 |

TABLE 1-continued

|  | Example No. | | | | | |
| --- | --- | --- | --- | --- | --- | --- |
|  | Ex. 1a | Ex. 1b[1,3] | Ex. 2 | Ex. 3 | Ex. 4a | Ex. 4b[1,3] |
| K-factor | 0.678 | 0.659 | 0.623 | 0.649 | 0.671 | 0.645 |
| 1-$C_6$= purity (% wt) | 99.5 | 99.3 | 99.6 | 99.0 | 98.7 | 99.5 |
| 1-$C_{12}$= purity (% wt) | 98.4 | 97.6 | 98.2 | 95.6 | 95.6 | 97.4 |

Experiments carried out at 50° C. in toluene, using 1-liter steel autoclave, unless indicated otherwise.
n.d. = not determined.
[1]Carried out at 70° C.
[2]Ethylene consumption derived from total product ($C_4$-$C_{100}$ olefins from regression analysis).
[3]Calculated on iron catalyst 3.
[4]Calculated on total iron content.

EXAMPLES 11-19

TABLE 2

Examples 11-19 have been carried out in a steel autoclave generally at 1.6 MPa ethylene pressure, using the amounts of iron catalyst precursor, co-catalyst and alternate co-catalyst, mentioned in Table 2.

It is clear from Examples 11-13 that ethylene oligomerisation takes place when either MAO or tri-isobutylaluminium (TIBA) is used to make the iron catalyst premix, but not when triethylaluminium (TEA) is used to make the premix.

The use of Lewis acids such as TIBA has a beneficial effect on the solubility of the Fe-catalyst system in toluene, whereas the catalytic activity and selectivity in ethylene oligomerisation are largely maintained.

It is remarkable that in the case of addition of a relatively small amount (Al:Fe=0.5) of triethylaluminium (TEA) (Example 12) the catalytic activity is completely lost, even after gradual increase of the amount of MAO to Al/Fe molar ratios as high as 250,000.

The use of a relatively small amount of TIBA (Example 13; Al:Fe=5), however, results in an inhomogeneous catalyst premix, which shows an activity and selectivity comparable to Example 11.

From Examples 14-19 it can be seen that TIBA may also be advantageously applied, if instead of the bis-(o-tolylimine)pyridine Fe-catalyst system derived from X, Fe-catalyst systems derived from catalyst precursors 3, 7 and 16' are used.

The use of small amounts of TIBA (Al:Fe=1) is advantageous, particularly, in continuous operation as a concentrated, but yet clear catalyst premix solution in toluene emerges, particularly, in the cases of catalyst precursors 3, 7 and 16'. This enables easy dosing of the corresponding Fe-catalyst premixes by pumping without clogging problems.

From Example 16 it may be inferred that the premix of the iron catalyst precursor 3 prepared with TIBA remains stable in an inert atmosphere for at least 5 days at room temperature, whereas the corresponding iron catalyst premixes prepared with MAO are either turbid from the start and/or have the tendency to form precipitates during storage under the same conditions.

Hence, the use of TIBA is particularly advantageous in continuous operation, where preferably stable concentrated and clear solutions have to be dosed to the reactor by pumping.

Moreover, the use of these relatively small amounts of TIBA (Al:Fe=1-5) does not compromise the iron catalyst's activity, K-factor and selectivity to α-olefins in ethylene oligomerisation, at least not to a large extent, as shown in Table 2.

TABLE 2

| | Example No. | | | | | | | | |
| --- | --- | --- | --- | --- | --- | --- | --- | --- | --- |
| | Ex. 11 | Ex. 12 | Ex. 13 | Ex. 14 | Ex. 15 | Ex. 16 | Ex. 17 | Ex. 18 | Ex. 19 |
| Iron Complex in Reactor/ Amount (nmol) | X[1)]/309 | X[1)]/73 | X[1)]/396 | 3[2)]/119 | 3[2)]/138 | 3[2,3)]/152 | 16'[4)]/56 | 16'[4)]/71 | 7[4)]/599 |
| Premix Co-catalyst/ Molar ratio Al/Fe | MAO/236 | TEA/0.5 | TIBA/5 | MAO/359 | TIBA/1 | TIBA/1 | MAO/418 | TIBA/1 | TIBA/1 |
| Reactor Co-catalyst | MAO | MAO | MAO | MAO | MAO | MAO | MAO | MAO | MAO |
| Overall molar ratio Al/Fe | 2000 | >2600[5)] | 2400 | 4200 | 3400 | 3200 | 8900 | 6700 | 800 |
| Reaction Time (min) | 34 | 60 | 35 | 53 | 58 | 60 | 31 | 39 | 37 |
| Ethene Pressure MPa (bar(a)) | 1.6 (16) | 1.6 (16) | 1.6 (16) | 3.1 (31) | 3.1 (31) | 3.1 (31) | 1.6 (16) | 1.6 (16) | 1.6 (16) |
| Ethene consumed (g) | 124.4 | 0.0 | 117.4 | 85.3[6)] | 78.7[6)] | 64.7[6)] | 52.3[6)] | 51.3[6)] | 58.7 |
| Isolated Product <C30 (g) | 101.7 | 0.0 | 102.8 | 74.4 | 70.5 | 59.5 | 47.8 | 47.9 | 33.9 |
| T.O.F (molC2=/ molFe*h) | 2.54E+07 | 0.0 | 1.83E+07 | 2.25E+07 | 1.82E+07 | 1.24E+07 | 3.61E+07 | 5.71E+07 | 5.63E+06 |
| K-factor | 0.72 | n.a. | 0.72 | 0.67 | 0.70 | 0.69 | 0.63 | 0.64 | 0.72 |

TABLE 2-continued

| | Example No. | | | | | | | | |
|---|---|---|---|---|---|---|---|---|---|
| | Ex. 11 | Ex. 12 | Ex. 13 | Ex. 14 | Ex. 15 | Ex. 16 | Ex. 17 | Ex. 18 | Ex. 19 |
| 1-$C_6$ = purity (% wt) | 99.4 | n.a. | 99.1 | 99.3 | 99.1 | 99.2 | 99.4 | 99.4 | 95.0 |
| 1-$C_{12}$ = purity (% wt) | 96.7 | n.a. | 94.0 | 97.2 | 96.2 | 96.4 | 97.4 | 97.3 | 96.8 |

Experiments carried out in 1-liter steel autoclave in toluene at 50° C., unless stated otherwise.
n.a. = not applicable;
n.d. = not determined,
TEA = triethylaluminium and TIBA = tri-isobutylaluminium.
[1]Catalyst prepared according to WO-A-99/02472.
[2]Carried out in 0.5-liter steel autoclave at 90° C.
[3]Catalyst premix stored under nitrogen at 20° C. for 5 days.
[4]Carried out in 0.5-liter steel autoclave at 70° C.
[5]MAO was gradually increased to an Al/Fe ratio of 250,000.
[6]From total oligomerisation product ($C_4$-$C_{100}$), which is assumed to be equal to ethylene intake.

We claim:

1. A bis-imine pyridine ligand of formula (II):

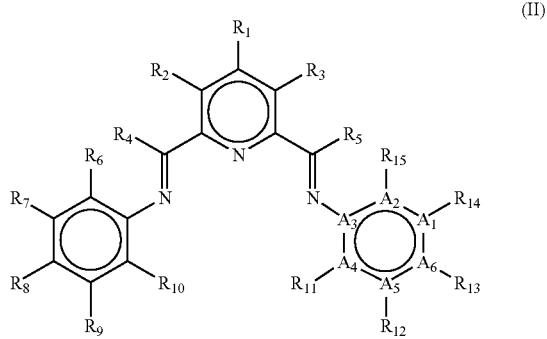

wherein $A_1$-$A_6$ are each, independently, carbon, nitrogen, oxygen, or sulphur; the atom group

may be optionally absent such that $A_1$ is directly bonded to $A_5$; and $R_1$-$R_{12}$, $R_{14}$-$R_{15}$ and, if present, $R_{13}$, are each, independently, hydrogen, optionally substituted hydrocarbyl, an inert functional group, or any two of $R_1$-$R_{15}$ vicinal to one another taken together may form a ring; with the proviso that when $A_1$-$A_5$, and $A_6$ if present, are all carbon, said atoms constitute the cyclopentadienyl or aryl part of a π-co-ordinated metal.

2. The ligand of claim 1 wherein $R_1$-$R_3$, $R_7$-$R_9$, $R_{12}$, $R_{14}$ and, if present, $R_{13}$, are each, independently, hydrogen, optionally substituted hydrocarbyl, an inert functional group, or any two of $R_1$-$R_3$, $R_7$-$R_9$, $R_{12}$-$R_{14}$ vicinal to one another taken together may form a ring; and a) $R_6$ is an inert functional group or an optionally substituted hydrocarbyl, and $R_{10}$, $R_{11}$, and $R_{15}$ are, independently, hydrogen or halide; or
b) $R_{11}$ is an inert functional group or an optionally substituted hydrocarbyl, and $R_6$, $R_{10}$, and $R_{15}$ are, independently, hydrogen or halide; or
c) $R_6$ and $R_{10}$ are each, independently, inert functional group or a primary or secondary carbon atom group, provided that $R_6$ and $R_{10}$ are not both a secondary carbon atom group and $R_{11}$ and $R_{15}$ are, independently, hydrogen or halide; or
d) $R_{11}$ and $R_{15}$ are each, independently, inert functional group or a primary or secondary carbon atom group, provided that $R_{11}$ and $R_{15}$ are not both a secondary carbon atom group and $R_6$ and $R_{10}$ are, independently, hydrogen or halide; or
e) $R_6$ is taken together with $R_7$ to form a ring, $R_{10}$ is a primary carbon atom group, an inert functional group, or hydrogen and $R_{11}$ and $R_{15}$ are, independently, hydrogen or halide; or
f) $R_{11}$ is taken together with $R_{12}$ to form a ring, $R_{15}$ is a primary carbon atom group, an inert functional group, or hydrogen and $R_6$ and $R_{10}$ are, independently, hydrogen or halide; or
g) $R_6$ and $R_{10}$ are taken together with $R_7$ and $R_9$, respectively, to form rings and $R_{11}$ and $R_{15}$ are, independently, hydrogen or halide;
h) $R_{11}$ and $R_{15}$ are taken together with $R_{12}$ and $R_{14}$, respectively, to form rings and $R_6$ and $R_{10}$ are, independently, hydrogen or halide.

3. The ligand of claim 1 wherein $R_{1-3}$ are hydrogen.
4. The ligand of claim 1 wherein $R_{4-5}$ are independently methyl, hydrogen or phenyl.
5. The ligand of claim 1 wherein $A_6$-$R_{13}$ is absent and $A_{1-5}$ are carbon atoms.
6. The ligand of claim 1 wherein $A_3$ is a nitrogen atom, $A_6$-$R_{13}$ is absent and $A_1$, $A_2$, $A_4$, $A_5$ are carbon atoms.
7. A mixed bis-imine pyridine $MX_n$ complex comprising a ligand wherein M is a metal atom selected from Fe or Co, n is 2 or 3, and X is halide, optionally substituted hydrocarbyl, alkoxide, amide, or hydride, wherein said ligand is a bis-imide pyridine ligand of formula (II):

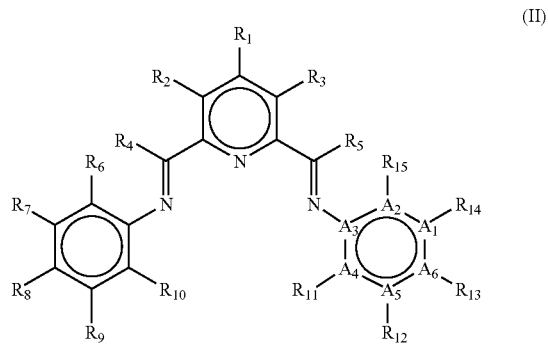

wherein $A_1$-$A_6$ are each, independently, carbon, nitrogen, oxygen, or sulphur; the atom group

may be optionally absent such that $A_1$ is directly bonded to $A_5$; and $R_1$-$R_{12}$, $R_{14}$-$R_{15}$ and, if present, $R_{13}$, are each, independently, hydrogen, optionally substituted hydrocarbyl, an inert functional group, or any two of $R_1$-$R_{15}$ vicinal to one another taken together may form a ring; with the proviso that when $A_1$-$A_5$, and $A_6$ if present, are all carbon, said atoms constitute the cyclopentadienyl or aryl part of a π-co-ordinated metal.

8. The mixed bis-imine pyridine $MX_n$ complex of claim 7 wherein wherein $R_1$-$R_3$, $R_7$-$R_9$, $R_{12}$, $R_{14}$ and, if present, $R_{13}$, are each, independently, hydrogen, optionally substituted hydrocarbyl, an inert functional group, or any two of $R_1$-$R_3$, $R_7$-$R_9$, $R_{12}$-$R_{14}$ vicinal to one another taken together may form a ring; and
   a) $R_6$ is an inert functional group or an optionally substituted hydrocarbyl, and $R_{10}$, $R_{11}$, and $R_{15}$ are, independently, hydrogen or halide; or
   b) $R_{11}$ is an inert functional group or an optionally substituted hydrocarbyl, and $R_6$, $R_{10}$, and $R_{15}$ are, independently, hydrogen or halide; or
   c) $R_6$ and $R_{10}$ are each, independently, inert functional group or a primary or secondary carbon atom group, provided that $R_6$ and $R_{10}$ are not both a secondary carbon atom group and $R_{11}$ and $R_{15}$ are, independently, hydrogen or halide; or
   d) $R_{11}$ and $R_{15}$ are each, independently, inert functional group or a primary or secondary carbon atom group, provided that $R_{11}$ and $R_{15}$ are not both a secondary carbon atom group and $R_6$ and $R_{10}$ are, independently, hydrogen or halide; or
   e) $R_6$ is taken together with $R_7$ to form a ring, $R_{10}$ is a primary carbon atom group, an inert functional group, or hydrogen and $R_{11}$ and $R_{15}$ are, independently, hydrogen or halide; or
   f) $R_{11}$ is taken together with $R_{12}$ to form a ring, $R_{15}$ is a primary carbon atom group, an inert functional group, or hydrogen and $R_6$ and $R_{10}$ are, independently, hydrogen or halide; or
   g) $R_6$ and $R_{10}$ are taken together with $R_7$ and $R_9$, respectively, to form rings and $R_{11}$ and $R_{15}$ are, independently, hydrogen or halide;
   h) $R_{11}$ and $R_{15}$ are taken together with $R_{12}$ and $R_{14}$, respectively, to form rings and $R_6$ and $R_{10}$ are, independently, hydrogen or halide.

9. The mixed bis-imine pyridine $MX_n$ complex of claim 7 wherein $R_{13}$ are hydrogen.

10. The mixed bis-imine pyridine $MX_n$ complex of claim 7 wherein $R_{4-5}$ are independently methyl, hydrogen or phenyl.

11. The mixed bis-imine pyridine $MX_n$ complex of claim 7 wherein $A_6$-$R_{13}$ is absent and $A_{1-5}$ are carbon atoms.

12. The mixed bis-imine pyridine $MX_n$ complex of claim 7 wherein $A_3$ is a nitrogen atom, $A_6$-$R_{13}$ is absent and $A_1$, $A_2$, $A_4$, $A_5$ are carbon atoms.

13. A mixed [bis-imine pyridine $MY_p$.Ln+][$NC^-$]$_q$ complex comprising a mixed bis-imide pyridine ligand wherein Y is a ligand which may insert an olefin; M is a metal atom selected from Fe or Co, $NC^-$ is a non-coordinating anion and p+q is 2 or 3, matching the formal oxidation state of said metal atom; L is a neutral Lewis donor molecule; and n=0, 1, or 2; wherein said mixed bis-imide pyridine ligand is a bis-imide pyridine ligand of formula (II):

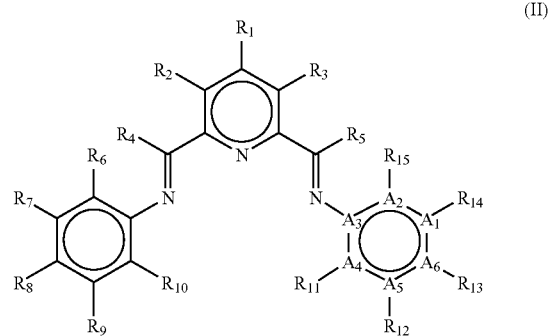

(II)

wherein $A_1$-$A_6$ are each, independently, carbon, nitrogen, oxygen, or sulphur; the atom group

may be optionally absent such that $A_1$ is directly bonded to $A_5$; and $R_1$-$R_{12}$, $R_{14}$-$R_{15}$ and, if present, $R_{13}$, are each, independently, hydrogen, optionally substituted hydrocarbyl, an inert functional group, or any two of $R_1$-$R_{15}$ vicinal to one another taken together may form a ring; with the proviso that when $A_1$-$A_5$, and $A_6$ if present, are all carbon, said atoms constitute the cyclopentadienyl or aryl part of a πco-ordinated metal.

14. The mixed [bis-imine pyridine $MY_p$.Ln+][$NC^-$]$_q$ complex of claim 13 wherein $R_1$-$R_3$, $R_7$-$R_9$, $R_{12}$, $R_{14}$ and, if present, $R_{13}$, are each, independently, hydrogen, optionally substituted hydrocarbyl, an inert functional group, or any two of $R_1$-$R_3$ $R_7$-$R_9$, $R_{12}$-$R_{14}$ vicinal to one another taken together may form a ring; and
   a) $R_6$ is an inert functional group or an optionally substituted hydrocarbyl, and $R_{10}$, $R_{11}$, and $R_{15}$ are, independently, hydrogen or halide; or
   b) $R_{11}$ is an inert functional group or an optionally substituted hydrocarbyl, and $R_6$, $R_{10}$, and $R_{15}$ are, independently, hydrogen or halide; or
   c) $R_6$ and $R_{10}$ are each, independently, inert functional group or a primary or secondary carbon atom group, provided that $R_6$ and $R_{10}$ are not both a secondary carbon atom group and $R_{11}$ and $R_{15}$ are, independently, hydrogen or halide; or
   d) $R_{11}$ and $R_{15}$ are each, independently, inert functional group or a primary or secondary carbon atom group, provided that $R_{11}$ and $R_{15}$ are not both a secondary carbon atom group and $R_6$ and $R_{10}$ are, independently, hydrogen or halide; or
   e) $R_6$ is taken together with $R_7$ to form a ring, $R_{10}$ is a primary carbon atom group, an inert functional group, or hydrogen and $R_{11}$ and $R_{15}$ are, independently, hydrogen or halide; or
   f) $R_{11}$ is taken together with $R_{12}$ to form a ring, $R_{15}$ is a primary carbon atom group, an inert functional group, or hydrogen and $R_6$ and $R_{10}$ are, independently, hydrogen or halide; or g) $R_6$ and $R_{10}$ are taken together with $R_7$ and $R_9$, respectively, to form rings and $R_{11}$ and $R_{15}$ are, independently, hydrogen or halide;

h) $R_{11}$ and $R_{15}$ are taken together with $R_{12}$ and $R_{14}$, respectively, to form rings and $R_6$ and $R_{10}$ are, independently, hydrogen or halide.

15. The mixed [bis-imine pyridine $MY_p.Ln+][NC^-]_q$ complex of claim 13 wherein $R_{1-3}$ are hydrogen.

16. The mixed [bis-imine pyridine $MY_p.Ln+][NC^-]_q$ complex of claim 13 wherein $R_{4-5}$ are independently methyl, hydrogen or phenyl.

17. The mixed [bis-imine pyridine $MY_p.Ln+][NC^-]_q$ complex of claim 13 wherein $A_6$-$R_{13}$ is absent and $A_{1-5}$ are carbon atoms.

18. The mixed [bis-imine pyridine $MY_p.Ln+][NC^-]_q$ complex of claim 13 wherein $A_3$ is a nitrogen atom, $A_6$-$R_{13}$ is absent and $A_1$, $A_2$, $A_4$, $A_5$ are carbon atoms.

19. A process for the production of alpha-olefins, which comprises contacting one or more mixed bis-imine pyridine $MX_n$ complexes comprising a ligand wherein M is a metal atom selected from Fe or Co, n is 2 or 3, and X is halide, optionally substituted hydrocarbyl, alkoxide, amide, or hydride, wherein said ligand is a bis-imide pyridine ligand of formula (II):

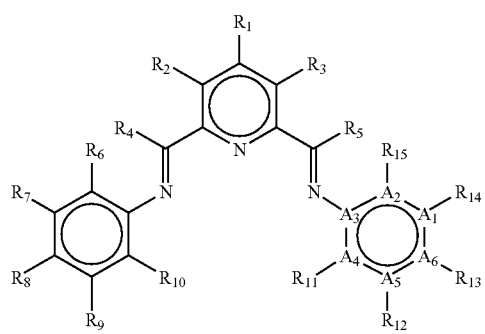

(II)

wherein $A_1$-$A_6$ are each, independently, carbon, nitrogen, oxygen, or sulphur; the atom group

may be optionally absent such that $A_1$ is directly bonded to $A_5$; and $R_1$-$R_{12}$, $R_{14}$-$R_{15}$ and, if present, $R_{13}$, are each, independently, hydrogen, optionally substituted hydrocarbyl, an inert functional group, or any two of $R_1$-$R_{15}$ vicinal to one another taken together may form a ring: with the proviso that when $A_1$-$A_5$, and $A_6$ if present, are all carbon, said atoms constitute the cyclopentadienyl or aryl part of a πco-ordinated metal; with ethylene and a second compound which is capable of transferring an optionally substituted hydrocarbyl or hydride group to a metal atom M selected from Fe or Co, and which is also capable of abstracting an $X^-$ group from said metal atom, at a temperature in the range of $-100°$ C. to $+300°$ C.

20. A process for the production of alpha-olefins, which comprises contacting one or more mixed bis-imine pyridine $MX_n$ complexes comprising a ligand wherein M is a metal atom selected from Fe or Co, n is 2 or 3, and X is halide, optionally substituted hydrocarbyl, alkoxide, amide, or hydride, wherein said ligand is a bis-imide pyridine ligand of formula (II):

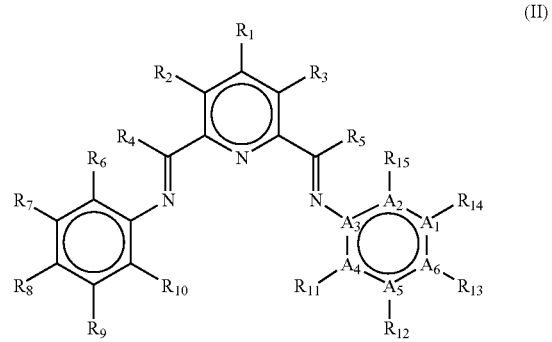

(II)

wherein $A_1$-$A_6$ are each, independently, carbon, nitrogen, oxygen, or sulphur; the atom group

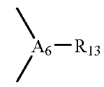

may be optionally absent such that $A_1$ is directly bonded to $A_5$; and $R_1$-$R_{12}$, $R_{14}$-$R_{15}$ and, if present, $R_{13}$, are each, independently, hydrogen, optionally substituted hydrocarbyl, an inert functional group, or any two of $R_1$-$R_{15}$ vicinal to one another taken together may form a ring; with the proviso that when $A_1$-$A_5$, and $A_6$ if present, are all carbon, said atoms constitute the cyclopentadienyl or aryl part of a πco-ordinated metal; with ethylene and a second compound which is capable of transferring an optionally substituted hydrocarbyl or hydride group to a metal atom M selected from Fe or Co, and a third compound which is capable of abstracting an $X^-$ group from said metal atom, at a temperature in the range of from $-100°$ C. to $+300°$ C.

21. A process for the production of alpha-olefins, which comprises contacting one or more mixed [bis-imine pyridine $MY_p.Ln+][NC^{-1}]_q$ complexes comprising a mixed bis-imide pyridine ligand wherein Y is a ligand which may insert an olefin; M is a metal atom selected from Fe or Co, $NC^-$ is a non-coordinating anion and p+q is 2 or 3, matching the formal oxidation state of said metal atom; L is a neutral Lewis donor molecule: and n=0, 1, or 2; wherein said mixed bis-imide pyridine ligand is a bis-imide pyridine ligand of formula (II):

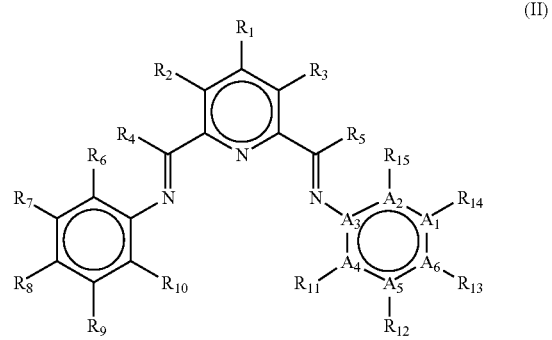

(II)

wherein $A_1$-$A_6$ are each, independently, carbon, nitrogen, oxygen, or sulphur; the atom group

may be optionally absent such that $A_1$ is directly bonded to $A_5$; and $R_1$-$R_{12}$, $R_{14}$-$R_{15}$ and, if present, $R_{13}$, are each, independently, hydrogen, optionally substituted hydrocarbyl, an inert functional group, or any two of $R_1$-$R_{15}$ vicinal to one another taken together may form a ring; with the proviso that when $A_1$-$A_5$, and $A_6$ if present, are all carbon, said atoms constitute the cyclopentadienyl or aryl part of a πco-ordinated metal; with ethylene at a temperature in the range of from −100° C. to +300° C.

* * * * *